United States Patent [19]
Naughton et al.

[11] Patent Number: 5,962,325
[45] Date of Patent: *Oct. 5, 1999

[54] THREE-DIMENSIONAL STROMAL TISSUE CULTURES

[75] Inventors: Gail K. Naughton, La Jolla; Brian A. Naughton, El Cajon, both of Calif.

[73] Assignee: Advanced Tissue Sciences, Inc., La Jolla, Calif.

[*] Notice: This patent is subject to a terminal disclaimer.

[21] Appl. No.: 09/157,306

[22] Filed: Sep. 18, 1998

Related U.S. Application Data

[60] Division of application No. 08/463,566, Jun. 5, 1995, which is a continuation-in-part of application No. 08/254,096, Jun. 6, 1994, abandoned, which is a continuation-in-part of application No. 08/131,361, Oct. 4, 1993, Pat. No. 5,443,950, which is a division of application No. 07/575,518, Aug. 30, 1990, Pat. No. 5,266,480, which is a division of application No. 07/402,104, Sep. 1, 1989, Pat. No. 5,032,508, which is a continuation-in-part of application No. 07/242,096, Sep. 8, 1988, Pat. No. 4,963,489, which is a continuation-in-part of application No. 07/038,110, Apr. 17, 1987, abandoned, which is a continuation-in-part of application No. 07/036,154, Apr. 3, 1987, Pat. No. 4,721,096, which is a continuation of application No. 06/853,569, Apr. 18, 1986, abandoned.

[51] Int. Cl.⁶ .............................. C12N 5/00; A61K 35/12; A01N 1/02; A61F 2/10
[52] U.S. Cl. ........................ 435/395; 424/572; 424/529; 424/530; 424/534; 424/574; 435/1.1; 435/325; 435/402; 435/405; 623/15
[58] Field of Search ........................ 435/1.1, 325, 395, 435/402, 405; 424/529, 530, 534, 572, 574; 623/15

[56] References Cited

U.S. PATENT DOCUMENTS

| | | | |
|---|---|---|---|
| 4,609,551 | 9/1986 | Caplan et al. | 424/95 |
| 4,721,096 | 1/1988 | Naughton et al. | 128/1 |
| 4,963,489 | 10/1990 | Naughton et al. | 435/240 |
| 5,032,508 | 7/1991 | Naughton et al. | 435/32 |
| 5,041,138 | 8/1991 | Vacanti et al. | 623/16 |
| 5,266,480 | 11/1993 | Naughton et al. | 435/240.243 |

OTHER PUBLICATIONS

Alexandrow et al. (1995) "Transforming Growth Factor β and Cell Cycle Regulation" *Cancer Research* 55:1452–1457.

(List continued on next page.)

*Primary Examiner*—Jeffrey Stucker
*Assistant Examiner*—Hankyel T. Park
*Attorney, Agent, or Firm*—Pennie & Edmonds LLP

[57] ABSTRACT

The present invention relates to a method of stimulating the proliferation and appropriate cell maturation of a variety of different cells and tissues in three-dimensional cultures in vitro using TGF-β in the culture medium. In accordance with the invention, stromal cells, including, but not limited to, chondrocytes, chondrocyte-progenitors, fibroblasts, fibroblast-like cells, umbilical cord cells or bone marrow cells from umbilical cord blood are inoculated and grown on a three-dimensional framework in the presence of TGF-β. Stromal cells may also include other cells found in loose connective tissue such as endothelial cells, macrophages/monocytes, adipocytes, pericytes, reticular cells found in bone marrow stroma, etc. The stromal cells and connective tissue proteins naturally secreted by the stromal cells attach to and substantially envelope the framework composed of a biocompatible non-living material formed into a three-dimensional structure having interstitial spaces bridged by the stromal cells. The living stromal tissue so formed provides the support, growth factors, and regulatory factors necessary to sustain long-term active proliferation of cells in culture and/or cultures implanted in vivo. When grown in this three-dimensional system, the proliferating cells mature and segregate properly to form components of adult tissues analogous to counterparts in vivo.

20 Claims, 26 Drawing Sheets

OTHER PUBLICATIONS

Barnard et al., 1990, "The cell biology of transforming growth factor β", Biochem. Biophys. Acta. 1032:79–87.

Campbell et al. (1991) "Human Articular Cartilage and Chondrocytes Produce Hempoietic Colony–Stimulating Factors in Culture in Response to IL–1" *The Journal of Immunology* 147:1238–1246.

Coffey et al., 1988, "Growth Modulation of Mouse Keratinocytes by Transforming Growth Factors," Cancer Res. 48:1596–1602.

Derynck et al., 1988, "A new type of transforming growth factor–β, TGF–β3," EMBO J. 7:3737–3743.

Gentry et al. (1987) "Type 1 Transforming Growth Factor Beta: Amplified Expression and Secretion of Mature and Precursor Polypeptides in Chinese Hamster Ovary Cells" *Molecular and Cellular Biology* 7(10):3418–3427.

Goey et al., 1989, "Inhibition of Early Murine Hemopoietic Progenitor Cell Proliferation After In Vivo Locoregional Administration of Transforming Growth Factor–β1," J. Immunol. 143:877–880.

Hamerman et al. (1986) "A Cartilage–Derived Growth Factor Enhances Hyaluronate Synthesis and Diminishes Sulfated Glycosaminoglycan Synthesis in Chondrocytes" *Journal of Cellular Physiology* 127:317–322.

Horton et al. (1989) "Transforming Growth Factor–Beta and Fibroblast Growth Factor Act Synergistically to Inhibit Collagen II Synthesis Through a Mechanism Involving Regulatory DNA Sequences" *Journal of Cellular Physiology* 141:8–15.

Ignotz et al. (1986) "Transforming Growth Factor–β Stimulates the Expression of Fibronectin and Collagen and Their Incorporation into the Extracellular Matrix" 261(9):4337–4345.

Jackson (1983) "Current Concepts Review Anthroscopic Surgery" *The Journal of Bone and Joint Surgery* 65–A(3):416–420.

Joyce et al., 1990, "Transforming Growth Factor–β and the Initiation of Chondrogenesis and Osteogenesis in the Rat Femur," J. Cell Biol. 110:2195–2207.

Lindahl et al. (1987) "Effects of growth hormone and insulin–like growth factor–I on colony formation of rabbit epiphyseal chondrocytes at different stages of maturation" *J. Endocr.* 115:263–271.

Madisen et al., 1988, "Transforming Growth Factor–β2: cDNA Cloning and Sequence Analysis," DNA 7:1–8.

Makower et al. (1989) "Effects of IGF–I, rGH, FGF, EGF and NCS on DNA–Synthesis, Cell Proliferation and Morphology of Chondrocytes Isolated from Rat Rib Growth Cartilage" *Cell. Biol. Int. Res.* 13:259–270.

Maor et al. (1989) "Human Growth Hormone Enhances Chondrogenesis and Osteogenesis in a Tissue Culture System of Chondroprogenitor Cells" *Endocrinology* 125(9):1239–1245.

Marquardt et al., 1987, "Complete Amino Acid Sequence of Human Transforming Growth Factor Type β2", Biol. Chem. 262:12127–12131.

Massaque, 1990, "The Transforming Growth Factor–β Family," Annu. Rev. Cell. Biol. 6:597–619.

McCurry et al. (1995) "Human complement regulatory proteins protect swine–to–primate cardiac xenografts from humoral injury" *Nature Medicine* 1:423–427.

McPherron and Lee, 1993, "GDF–3 and GDF–9: Two New Members of the Transforming Growth Factor–β Superfamily Containing a Novel Pattern of Cysteines," J. Biol. Chem. 268:3444–3449.

McQuillan et al. (1986) "Stimulation of proteoglycan biosynthesis by serum and insulin–like growth factor–I in cultured bovine articular cartilage" *Biochem. J.* 240:423–430.

Mombaerts et al. (1991) "Creation of a large genomic deletion at the T–cell antigen receptor β–subunit locus in mouse embryonic stem cells by gene targeting" *Proc. Natl. Acad. Sci. USA* 88:3084–3087.

Mow et al. (1984) "Fluid Transport and Mechanical Properties of Articular Cartilage: A Review" *J. Biomechanics* 17(5):377–394.

Mustoe et al. (1987) "Accelerated Healing of Incisional Wounds in Rats Induced by Transforming Growth Factor–β" *Science* 237:1333–1335.

Noda and Camilliere, 1989, "In Vivo Stimulation of Bone Formation by Transforming Growth Factor–β," Endocrinnol. 124:2991–2995.

Nugent and Edelman, 1992, "Transforming Growth Factor β1 Stimulates the Production of Basic Fibroblast Growth Factor Binding Proteoglycans in Balb/c3T3 Cells," J. Biol. Chem. 267:21256–21264.

Osborn et al. (1989) "Growth Factor Stimulation of Adult Articular Cartilage" *Journal of Orthopaedic Research* 7:35–42.

Prins et al. (1982) "Effect of Purified Growth Factors on Rabbit Articular Chondrocytes in Monolayer Culture" *Arthritis and Rheumatism* 25(10):1228–1238.

Roberts et al. (1981) "New class of transforming growth factors potentiated by epidermal growth factor: Isolation from non–neoplastic tissues" *Proc. Natl. Acad Sci. USA* 78(9):5339–5343.

Roberts et al., 1985, "Type β transforming growth factor: A bifunctional regulator of cellular growth," Proc. Natl. Acad. Sci. USA 82:119–123.

Rosen et al. (1988) "Transforming Growth Factor–Beta Modulates the Expression of Osteoblast and Chondroblast Phenotypes In Vitro" *Journal of Cellular Physiology* 134:337–346.

Selden et al. (1987) "Implantation of Genetically Engineered Fibroblasts into Mice: Implications for Gene Therapy" *Science* 236:714–718.

Seyedin et al., 1987, "Cartilage–inducing Factor–B Is a Unique Protein Structurally and Functionally Related to Transforming Growth Factor–β," J. Biol. Chem. 262:1946–1949.

Tiku et al. (1990) "Production of Hydrogen Peroxide by Rabbit Articular Chondrocytes" *The Journal of Immunologies* 145(2):690–696.

Tucker et al. (1984) "Specific binding to cultured cells of $^{125}$I–labeled type β transforming growth factor from human platelets" *Proc. Natl. Acad Sci. USA* 81:6757–6761.

Tyler (1985) "Chrondrocyte–mediated depletion of articular cartilage proteoglycans in vitro *Biochem J.* 225:493–507.

Tyler (1985) "Articular cartilage cultured with catabolin (pig interleukin 1) synthesizes a decreased number of normal proteoglycan molecules *Biochem J.* 227:869–878.

Wozney et al., 1988, "Novel Regulators of Bone Formation: Molecular Clones and Activities," Science 242:1528–1534.

Yaron et al. (1989) "Some Recombinant Human Cytokines Stimulate Glycosaminoglycan Synthesis in Human Synovial Fibroblast Cultures and Inhibit it in Human Articular Cartilage Cultures" *Arthritis and Rheumatism* 32(2):173–180.

STATIC
45mg/cc (N.H.P.)

4 wks
[end 4/18/94]

CBR
45mg/cc (N.H.P.)

4 wks
[end: 4/15/94]

THREE-DIMENSIONAL STROMAL TISSUE CULTURES

The present application is a divisional of U.S. patent application Ser. No. 08/463,566, filed Jun. 5, 1995, currently allowed, which in turn is a continuation-in-part of application Ser. No. 08/254,096 filed Jun. 6, 1994 (abandonded); which is a continuation-in-part of application Ser. No. 08/131,361 filed Oct. 4, 1993 (U.S. Pat. No. 5,443,950); which is a divisional of application Ser. No. 07/575,518 filed Aug. 30, 1990 (U.S. Pat. No. 5,266,480); which is a divisional of application Ser. No. 07/402,104 filed Sep. 1, 1989 (U.S. Pat. No. 5,032,508); which is a continuation-in-part of application Ser. No. 07/242,096 filed Sep. 8, 1988 (U.S. Pat. No. 4,963,489); which is a continuation-in-part of application Ser. No. 07/038,110 filed Apr. 17, 1987 (abandoned); which is a continuation-in-part of application Ser. No. 07/036,154 filed Apr. 3, 1987 (U.S. Pat. No. 4,721,096); which is a continuation of application Ser. No. 06/853,569 filed Apr. 18, 1986 (abandoned), each of which is incorporated by reference herein in its entirety.

TABLE OF CONTENTS

1. INTRODUCTION
2. BACKGROUND OF THE INVENTION
    2.1. Growth Factors and Hormones
        2.1.1. Transforming Growth Factor-β
        2.1.2. Insulin-like Growth Factors I and II (IGF-I and IGF-II)
        2.1.3. Growth Hormone (GH)
        2.1.4. Other Growth Factors
3. SUMMARY OF THE INVENTION
4. BRIEF DESCRIPTION OF THE DRAWING
5. DETAILED DESCRIPTION OF THE INVENTION: THE STIMULATION OF CELL PROLIFERATION AND APPROPRIATE CELL MATURATION
    5.1. Establishment Of Three-dimensional Stromal Tissue
    5.2. Uses of the Three-Dimensional Culture System
        5.2.1. Transplantation In Vivo
        5.2.2. Screening Effectiveness and Cytotoxicity of Compounds In Vitro
        5.2.3. Genetically Engineered Cartilage
        6. EXAMPLE: THREE-DIMENSIONAL CHONDROCYTE CULTURE SYSTEM
    6.1. Material and Methods
        6.1.1. Growth Factors
        6.1.2. Cells
        6.1.3. Cell Seeding
        6.1.4. Histology and Immunohistochemistry
        6.1.5. Immunoblotting
        6.1.6. Quantitation of Collagen and GAG
        6.1.7. Northern Blot Analysis
    6.2. Effect of Ethylene Oxide or Electron Beam Sterilization on Rabbit Chondrocyte Cultures
    6.3. Results
        6.3.1. Effect of Ethylene Oxide or Electron Beam Sterilization on Rabbit Chondrocyte Cultures
7. Effect of TGF-β on Growth of Bovine Chondrocytes in Monolayer Culture and on Three-Dimensional Frameworks With Or Without Ascorbate
    7.1. RESULTS
        7.1.1. Effect of TGF-β on Growth of Bovine Chondrocytes in Monolayer Culture and on Three-Dimensional Frameworks With Or Without Ascorbate
    8. Cartilage Production by Rabbit Chondrocytes on Polyglycolic Acid Frameworks in a Closed Bioreactor System
        8.1. Results
            8.1.1. Cartilage Production by Rabbit Chondrocytes on Polyglycolic Acid Frameworks in a Closed Bioreactor System

1. INTRODUCTION

The invention relates to growing stromal cells, such as chondrocytes, progenitor-chondrocytes, fibroblasts and/or fibroblast-like cells on a three-dimensional scaffold or framework in vitro under conditions which enhance the formation of cartilage in culture. A variety of biodegradable and nonbiodegradable matrices treated with sterilizing agents and/or procedures can be used as the scaffold in accordance with the invention. A variety of culture conditions can be adjusted, including the control of physical conditions such as pressure and/or the addition of growth factors. Additionally, the cultured cells can be genetically engineered to express gene products beneficial to growth, transplantation and/or amelioration of disease conditions.

The resulting three-dimensional cultures and biological replacement cartilage tissue constructs have a variety of applications ranging from transplantation or implantation in vivo, to screening the effectiveness of cytotoxic compounds and pharmaceutical agents in vitro. The invention is demonstrated by way of examples describing the three-dimensional culture of chondrocytes.

2. BACKGROUND OF THE INVENTION

Articular cartilages are responsible for providing moveable joints the ability for smooth gliding motion. The articular cartilages are firmly attached to the underlying bones and measure less than 5 mm in thickness in human joints, with considerable variation depending on joint and site within the joint. The articular cartilages are aneural, avascular, and alymphatic. In adult humans, they derive their nutrition by a double diffusion system through the synovial membrane and through the dense matrix of the cartilage to reach the chondrocyte.

The biochemical composition of articular cartilage includes up to 65–80% water (depending on the cartilage), with collagen as the most prevalent organic constituent. Articular cartilage consists of highly specialized chondrocytes surrounded by a dense extracellular matrix consisting mainly of type II collagen, proteoglycan and water. Collagen (mainly type II) accounts for about 15–25% of the wet weight and about half the dry weight, except in the superficial zone where it accounts for most of the dry weight. Its concentration is usually progressively reduced with increasing depth from the articular surface. The proteoglycan content accounts for up to 10% of the wet weight or about a quarter of the dry weight. Proteoglycans consist of a protein core to which linear sulfated polysaccharides are attached, mostly in the form of chondroitin sulfate and keratin sulfate. In addition to type II collagen, articular collagen contains several other collagen types (IV, V, IX and X) with distinct structures. There are a variety of interactions between these individual macromolecules, which include both noncovalent associations between proteoglycans and collagens, and covalent bonds between different collagen species. Resistance of the extracellular matrix to water flow gives cartilage its ability to dispense high joint loads. It absorbs shock and minimizes stress on subchondral bone (Mow et al., 1984, J. Biomech. 17:377–394). Adult cartilage and bone have a limited ability of repair.

Damage of cartilage produced by disease, such as rheumatoid and/or osteoarthritis, or trauma can lead to serious physical deformity and debilitation. As human articular cartilage ages, its tensile properties change. The superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not decrease. These observations indicate that there are changes in mechanical and, hence, structural organization of cartilage with aging that, if sufficiently developed, can predispose cartilage to traumatic damage. In osteoarthritic cartilage there is excessive damage to type II collagen, resulting in crimping of collagen fibrils. In rheumatoid arthritis, the combined actions of free radicals and proteinases released from polymorpholeukocytes cause much of the damage seen at the articular surface. (Tiku et al., 1990, J. Immunol. 145:690–696). Induction of cartilage matrix degradation and proteinases by chondrocytes is probably induced primarily by interleukin-1 (IL-1) or tumor necrosis factor-α (TNF-α) (Tyler, 1985, Biochem. J. 225:493–507).

The current therapy for loss of cartilage is replacement with a prosthetic material, for example, silicone for cosmetic repairs, or metal alloys for joint relinement. Placement of prosthetic devices is usually associated with loss of underlying tissue and bone without recovery of the full function allowed by the original cartilage. Serious long-term complications associated with the presence of a permanent foreign body can include infection, erosion and instability.

Use of sterilized bone or bone powder or surgical steel seeded with bone cells which were eventually implanted have been largely unsuccessful because of the non-degradable nature of the cell support. According to one procedure fibroblasts are exposed in vitro for a minimum of three days, to a soluble bone protein capable of stimulating in vitro and/or in vivo a chondrogenic response. The activated fibroblasts are then transferred in vivo by combining them with a biodegradable matrix, or by intra-articular injection or attachment to allografts and prosthetic devices. The disadvantage of this method is that chondrogenesis is not allowed to develop in the short-term cultures and there is an unduly heavy reliance for cartilage synthesis by the exposed fibroblasts at the implant site. Caplan, A., U.S. Pat. No. 4,609,551, issued Sep. 2, 1986.

U.S. Pat. No. 5,041,138 to J. P. Vacanti et al., issued Aug. 20, 1991, describes growth of cartilaginous structures seeding chondrocytes on biodegradable matrices for subsequent implantation in vivo. Although this system offers the advantage of a greater surface area and exposure to nutrients, the conditions employed for culturing the chondrocytes are routine and no efforts have been made to optimize the conditions for the chondrocytes to produce collagen and other cartilage-type macromolecules.

2.1. Growth Factors and Hormones

Growth factors have paracrine or autocrine effects on cell metabolism and can retard or enhance chondrocyte division, and matrix synthesis, and degradation.

2.1.1. Transforming Growth Factor-β

TGF-β refers to a growing family of related dimeric proteins which regulate the growth and differentiation of many cell types (Barnard et al., 1990, Biochem. Biophys. Acta. 1032:79–87; Massague, 1990, Annu. Rev. Cell. Biol. 6:597–619; Roberts and Sporn, 1990, pp. 419–472 M. B. Sporn and A. B. Roberts (eds.), Peptide Growth Factors and Their Receptors I, Springer-Verlag, Berlin). Members of this family include TGFβ-1 (Derynck et al., 1985, Nature 316:701–705; Moses et al., 1981, Cancer Res. 41:2842–2848; Roberts et al., 1981, Proc. Natl. Acad. Sci. USA 78, 5339–5343; Sharples et al., 1987, DNA 6:239–244), TGF-β2 (DeMartin et al., 1987, EMBO J. 6:3676–3677; Hanks et al., 1988, Proc. Natl. Acad. Sci. USA 85, 79–82; Ikeda et al., 1987, Biochemistry 26, 2406–2410; Madisen et al., 1988, DNA 7, 1–8; Marquardt et al., 1987, Biol. Chem. 262:12127–12131, Seyedin et al., 1987, J. Biol. Chem. 262:1946–1949), TGF-β3 (Derynck et al., 1988, EMBO J. 7:3737–3743; Jakowlew et al., 1988, Endocrinnol. 2, 747–755, TGF-β4 (Jakowlew et al., 1988, Mol. Endocrinnol. 2:1064–1069), TGF-β5 (Kondaiah et al., 1990, J. Biol. Chem. 265:1089–1093), and the more distantly related Mullerian inhibitory substance (Cate et al., 1986, Cell. 45:685–698), the inhibins (Mason et al., 1985, Nature 318:659–663), the bone morphogenetic proteins (Wozney et al., 1988, Science 242:1528–1534) and OP-1 (Özkaynak et al., 1990, EMBO J. 9:2085–2093). Newly discovered members include OP-2 (Özkaynak et al., 1992, J. Biol. Chem. 267:25220–25227), GDF-1 (Lee, 1990, Mol. Endocrinnol. 4:1034–1040); GDF-3 and GDF-9 (McPherron and Lee, 1993, J. Biol. Chem. 268:3444–3449) and Nodal (Zhou et al., 1993, Nature 361:543–546).

TGF-β was first characterized for its effects on cell proliferation. It both stimulated the anchorage-independent growth of rat kidney fibroblasts (Roberts et al., 1981), and inhibited the growth of monkey kidney cells (Tucker et al., 1984, Proc. Natl. Acad. Sci. USA 81:6757–6761). Since then, it has been shown to have many diverse biological effects: it stimulates bone formation (Noda and Camilliere, 1989, Endocrinnol. 124:2991–2995; Joyce et al., 1990, J. Cell. Biol. 110:2195–2207; Marcelli et al., 1990, J. Bone Mineral Res. 5:1087–1096; Beck et al., 1991, J. Bone Mineral Res. 6:961; Mackie and Trechsel, 1990, J. Cell. Biol. 110, 2195–2207), induces rat muscle cells to produce cartilage-specific macromolecules (Seyedin et al., 1984, J. Biol. Chem. 261:5693–5695; Seyedin et al., 1986, J. Biol. Chem. 261:5693–5695; and Seyedin et al., 1987, J. Biol. Chem. 262:1946–1949), inhibits the growth of early hematopoietic progenitor cells (Goey et al., 1989, J. Immunol. 143:877–880), T cells (Kehrl et al., 1986, J. Exp. Med. 163:1037–1050), B cells (Kasid et al., 1988, J. Immunol. 141, 690–698), mouse keratinocytes (Pietenpol et al., 1990, Cell 61:777–785; Coffey et al., 1988, Cancer Res. 48:1596–1602) and several human cancer cell lines (Roberts et al., 1985, Proc. Natl. Acad. Sci. USA 82:119–123; Ranchalis et al., 1987, Biophys. Res. Commun. 148:783–789). It increases the synthesis and secretion of collagen and fibronectin (Ignotz and Massague, 1986, J. Biol. Chem. 261:4337–4345; Centrella et al., 1987, J. Biol. Chem. 262:2869–2874; Malemud et al., 1991, J. Cell Physio. 149:152–159; Galéra et al., 1992, J. Cell Physio. 153:596–606; Phillips et al., 1994, Soc. Inv. Derm. 103–2:228–232), accelerates healing of incisional wounds (Mustoe et al., 1987, Science 237:1333–1335), suppresses casein synthesis in mouse mammary explants (Robinson et al., 1993, J. Cell. Biol. 120:245–251), inhibits DNA synthesis and phosphorylation of pRb in rat liver epithelial cells (Whitson and Itakura, 1992, J. Cell. Biochem. 48:305–315), stimulates the production of BFGF binding proteoglycans (Nugent and Edelman, 1992, J. Biol. Chem. 267:21256–21264), modulates phosphorylation of the EGF receptor and proliferation of epidermoid carcinoma cells (Goldkorn and Mendelsohn, 1992, Cell Growth and Differentiation) and can lead to apoptosis in uterine epithelial cells (Rotello et al., 1991, Proc. Natl. Acad. Sci. USA 88:3412–3415), cultured hepatocytes and regressing liver (Oberhammer et al., 1992, Proc. Natl. Acad. Sci. USA 89:5408–5412). It can mediate cardioprotection against reperfusion injury (Lefer et al., 1990, Science 249, 61–64) by inhibiting neutrophil adherence to endothelium (Lefer et al., 1993, Proc. Natl. Acad. Sci. USA 90:1018–1022), and it protects against experimental autoimmune diseases in mice (Kuruvilla et al., 1991, Proc. Natl. Acad. Sci. USA 88:2918–2921).

In contrast to the foregoing reports of the ability of TGF-β to induce the production of cartilage-specific macromolecules in muscle cells and chondrocytes, TGF-β was found to act synergistically with fibroblast growth factor to inhibit the synthesis of collagen type II by chicken sternal chondrocytes (Horton et al., 1989, J. Cell Physio. 141:8–15) and TGF-β inhibited production of type II collagen in rat chondrocytes (Rosen et al., 1988, J. Cell Physio. 134:337–346). In fact, TGF-β has emerged as the prototypical inhibitor of the proliferation of most normal cell types in culture as well as in vivo, exhibiting a remarkable diversity of biological activity (Alexandrow, M. G., and Moses, H. L., 1995, Cancer Res. 55:1452–1457).

TGF-β1 has been purified from human and porcine blood platelets, Assoian et al., 1983, from human placenta, Frolick et al., 1983, and recombinant TGF-β1 is currently available, Gentry et al., 1988, Mol. Cell. Biol. 7:3418–3427.

2.1.2. Insulin-like Growth Factors I and II (IGF-I and IGF-II)

Insulin alone is much less potent than IGF-I in stimulating collagen matrix synthesis. Insulin, however, enhances proteoglycan synthesis in the presence of a low concentration of serum (1%). IGF-I, previously designated somatomedin c, is a potent inducer of collagen and proteoglycan synthesis in vitro. (Lindahl et al., 1987, J. Endocrinol. 115:263–271; Markower et al., 1989, Cell. Biol. Int. Rep. 13:259–270).

IGF-II stimulates DNA and RNA synthesis and is more potent than IGF-I in stimulating clonal growth in fetal cells, whereas IGF-I is more effective on adult chondrocytes. IGF-II can stimulate proteoglycan synthesis, but, like insulin, is much less effective than IGF-I (McQuillan et al., 1986, Biochem. J. 240:423–430).

2.1.3. Growth Hormone (GH)

Parenteral administration of GH can stimulate localized growth plate development in vivo. Hypophysectomy leads to disappearance of IGF-I in growth plate chondrocytes, indicating a cessation of synthesis. On the other hand, treatment with GH, systemically or locally, results in the appearance of IGF-I. Reports of direct stimulatory effects of GH on cell growth in vitro (Maro et al., 1989, Endocrinnology 125:1239–1445) conflict with reports that it has no effect (Burch et al., 1985, J. Clin. Endocrinnol. Metab. 60:747–750).

2.1.4. Other Growth Factors

Epidermal growth factor (EGF) alone has no effect on chondrocyte proliferation. Together with insulin, EGF synergistically stimulates proteoglycan synthesis and induces proliferation of chondrocytes. (Osborn et al., 1989, J. Orthop. Res. 7:35–42). Basic fibroblast growth factor (bFGF) inhibits proteoglycan synthesis in fetal articular cartilage (Hamerman et al., 1986, J. Cell. Physiol. 127:317–322), but it appears to function additively with IGF-I in adult articular cartilage and stimulates proteoglycan synthesis (Osborn, K. D., et al., 1989, J. Orthop. Res. 7:35–42). Platelet-derived growth factor (PDGF) also enhances proteoglycan synthesis (Prins et al., 1982, Arthritis Rheum. 25:1228–1238).

3. SUMMARY OF THE INVENTION

The present invention relates to the growth and preparation of cartilage in vitro which can be used for a variety of purposes in vivo. In accordance with the invention, stromal cells which elaborate cartilage-specific macromolecules and extracellular matrix proteins, are inoculated and grown on three-dimensional frameworks or biodegradable scaffolds. The stromal cells, which are inoculated onto the scaffold, may include chondrocytes, chondrocyte-progenitors, fibroblasts, fibroblast-like cells and/or cells capable of producing collagen type II and other collagen types, and proteoglycans which are typically produced in cartilaginous tissues (See Table I, infra). The stromal cells and connective tissue proteins secreted by the stromal cells attach to and substantially envelope the three-dimensional framework or construct, composed of a biocompatible non-living material formed into a three-dimensional structure, having interstitial spaces bridged by the stromal cells. The living stromal tissue so formed provides the support, growth factors, and regulatory factors necessary to sustain long-term active proliferation of stromal cells in culture and/or cultures implanted in vivo. When grown in this three-dimensional system, the proliferating cells mature and segregate properly to form components of adult tissue analogous to counterparts in vivo.

In another embodiment of the invention, the stromal cells are inoculated and grown on a three-dimensional framework placed in any container that can be manipulated to allow intermittent pressure changes or in a bioreactor system specially designed for the in vitro production of cartilage tissue constructs, which allows for pressurization of the chamber during growth and an adequate supply of nutrients to stromal cells by convection.

In yet another embodiment of the invention, the stromal cells are stimulated to produce cartilage using exogenously added growth factors, e.g., TGF-β with or without ascorbate, in culture. Alternatively, the stromal cells can be genetically engineered to express the genes for specific types of TGF-β (e.g., TGF-$β_1$) for successful and/or improved turnover of cartilage production post-transplantation.

In yet another embodiment of the invention, the stromal cells can be genetically engineered to express a gene product beneficial for successful and/or improved transplantation. For example, the stromal cells can be genetically engineered to express anti-inflammatory gene products to reduce the risk of degenerative diseases like rheumatoid arthritis resulting in failure of cartilage due to inflammatory reactions; e.g., the stromal cells can be engineered to express peptides or polypeptides corresponding to the idiotype of neutralizing antibodies for granulocyte-macrophage colony stimulating factor (GM-CSF), tumor necrosis factor (TNF), interleukin-2 (IL2), or other inflammatory cytokines and mediators. Preferably, the cells are engineered to express such gene products transiently and/or under inducible control during the post-operative recovery period, or as a chimeric fusion protein anchored to the stromal cell, e.g., a chimeric molecule composed of an intracellular and/or transmembrane domain of a receptor or receptor-like molecule, fused to the gene product as the extracellular domain.

In another alternative embodiment, the stromal cells can be genetically engineered to "knock out" expression of factors that promote rejection or degenerative changes in articular cartilage due to aging, rheumatoid disease or inflammation. For example, expression of pro-inflammatory mediators such as GM-CSF, TNF, IL-1, IL-2 and cytokines can be knocked out in the stromal cells to reduce the risk of inflammation. Likewise, the expression of MHC class II molecules can be knocked out in order to reduce the risk of rejection of the cartilage graft.

In yet another embodiment of the invention, the three-dimensional culture system of the invention may afford a vehicle for introducing genes and gene products in vivo to assist or improve the results of the transplantation and/or the use in gene therapies. For example, genes that prevent or ameliorate symptoms of degenerative changes in cartilage such as rheumatoid disease or inflammatory reactions and bone resorption, may be underexpressed or overexpressed in disease conditions and/or due to aging. Thus, the level of gene activity in the patient may be increased or decreased, respectively, by gene replacement therapy by adjusting the level of the active gene product in genetically engineered stromal cells.

In a specific embodiment exemplified by the examples in Sections 6–8, infra, chondrocytes from articular cartilage of New Zealand rabbits or cows were grown in culture in monolayer or on three-dimensional biodegradable, biocompatible fibrous framework or scaffold formed of sterilized polymers such as polyglycolic acid, polylactic acid or other polymers. The frameworks were designed to allow adequate nutrient and gas exchanges to the cells until engraftment at the site of engraftment takes place. Particular benefits were achieved by maintaining the cultures under sterile conditions without inhibiting the growth of cartilage in biodegradable polymers sterilized by chemical methods or radiation. Exogenous TGF-$\beta_1$ was added to the three-dimensional cultures to achieve a greatly increased proliferation and differentiation of chondrocyte cells. The cultured cartilage was characterized by analyzing the cartilage constructs for glycosaminoglycan, collagen I and II by histology and immunohistochemistry, biochemical quantitation, Northern-Blot analysis and immunoblotting.

4. BRIEF DESCRIPTION OF THE DRAWING

Figure 10:
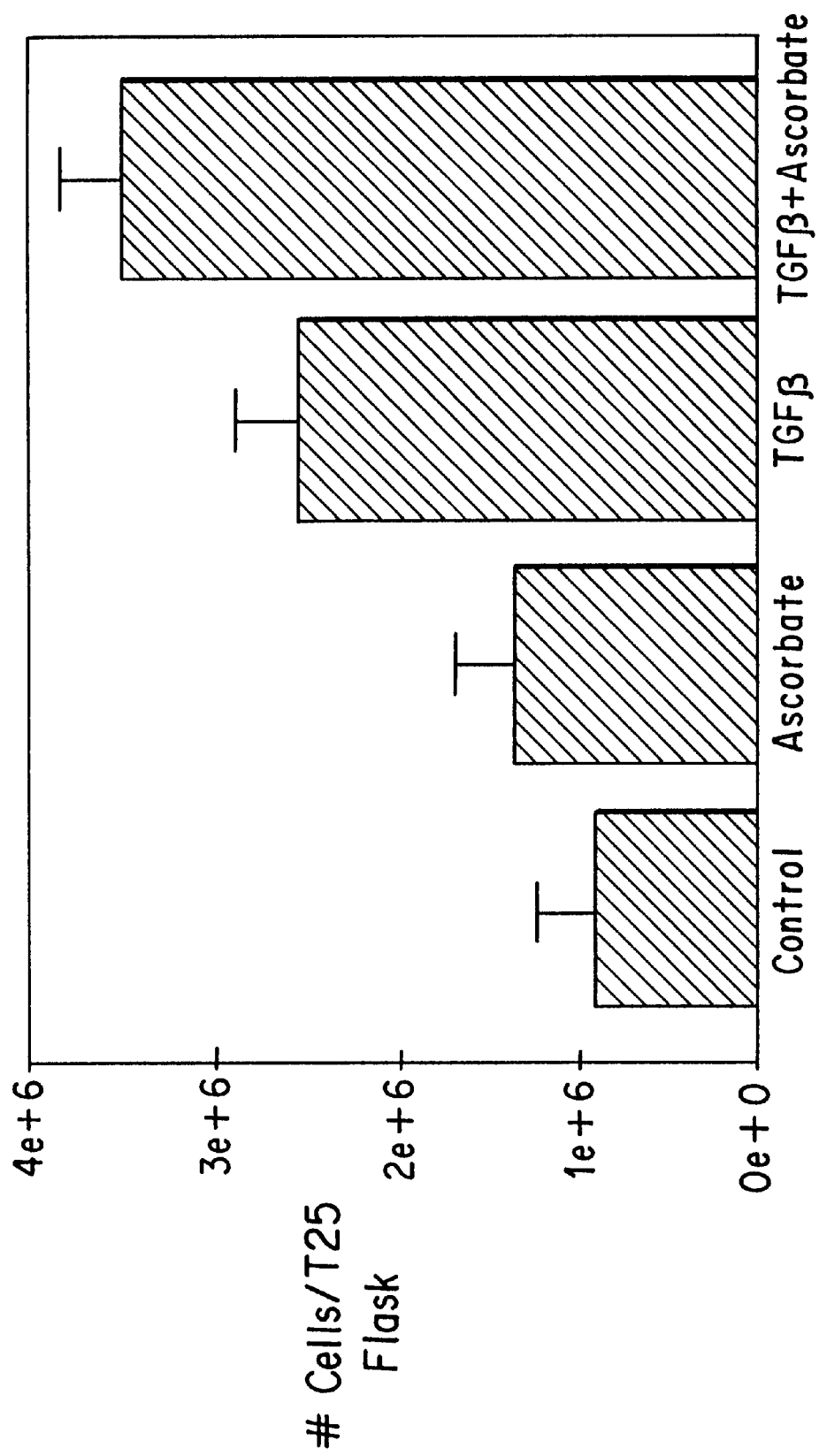

FIG. 10: TGF-β and ascorbate increase the proliferation of bovine articular chondrocytes.

Figure 11:
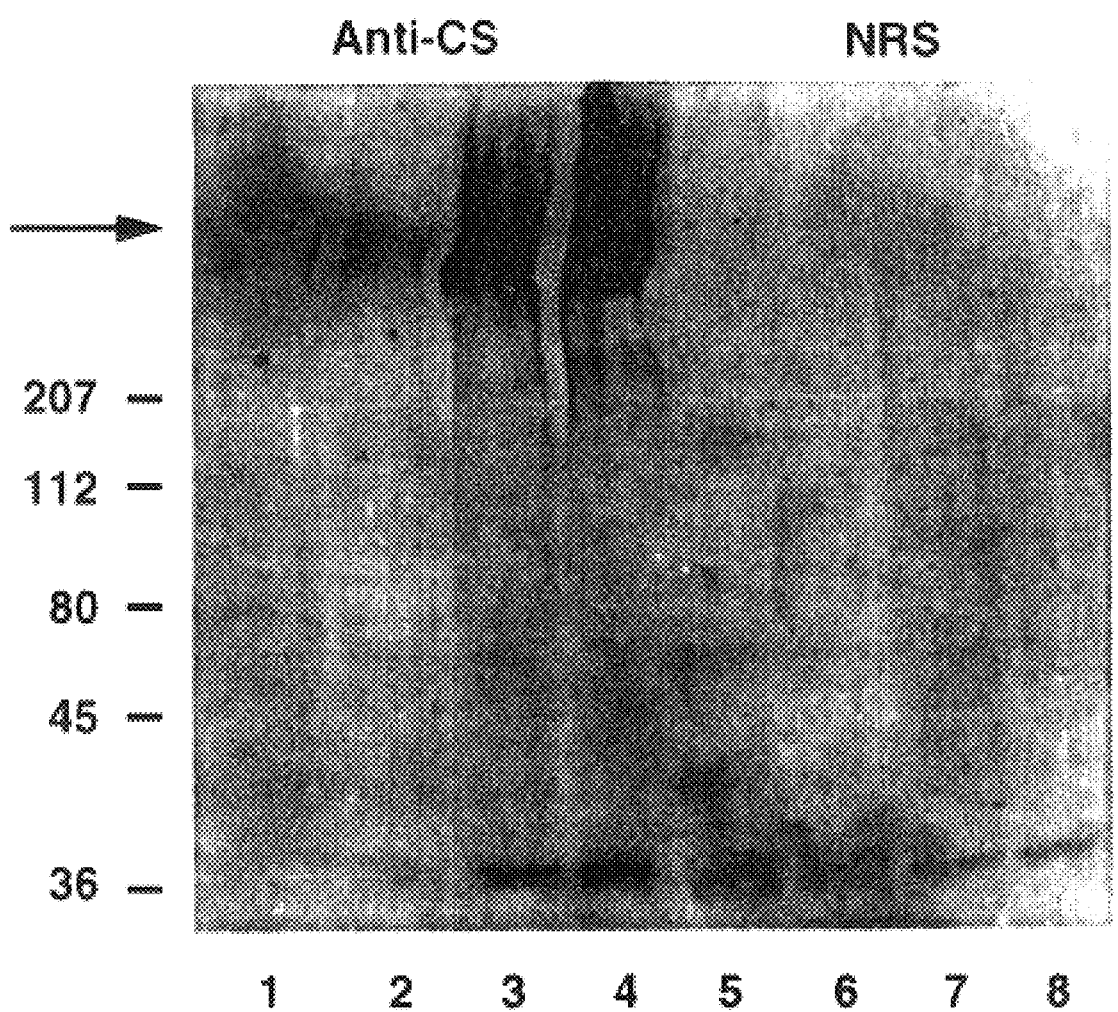

FIG. 11: Detection of collagen type II and GAGs in bovine articular chondrocyte lysates.

A. Bovine articular chondrocytes were grown in complete media containing no additives (lanes 1 and 5), ascorbate (50 ug/ml, lanes 2 and 6), TGF-β (20 ng/m, lanes 3 and 7), or TGF-β+ascorbate (lanes 4 and 8). Cell lysates were prepared, fractionated by SDS-PAGE and analyzed by immunoblotting using anti-chondroitin sulfate antibody (anti-CS; lanes 1–4) or normal rabbit serum (NRS; lanes 5–8).

Figure 12A:
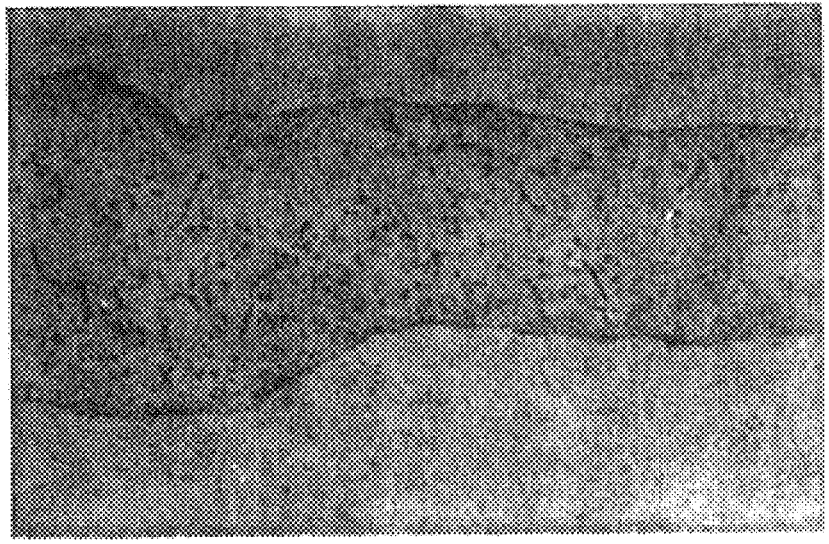
Figure 12B:
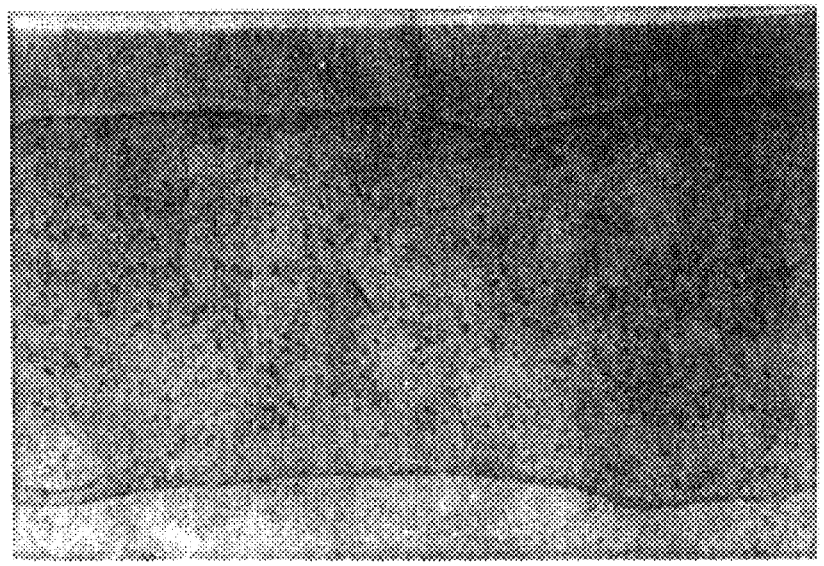
Figure 12C:
Figure 12D:
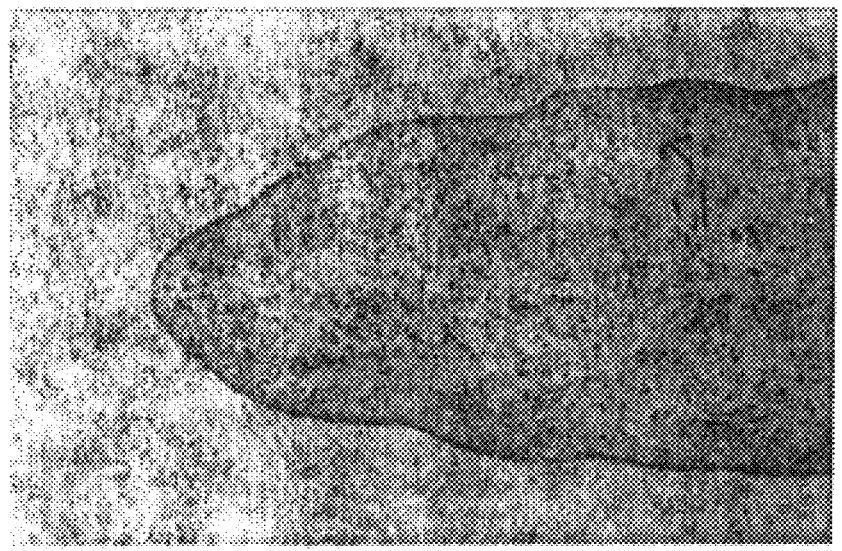
Figure 12E:
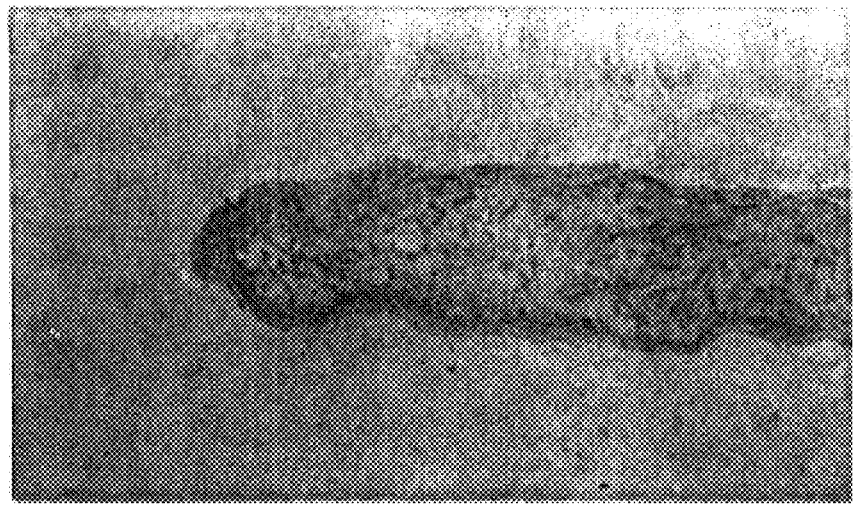
Figure 12F:
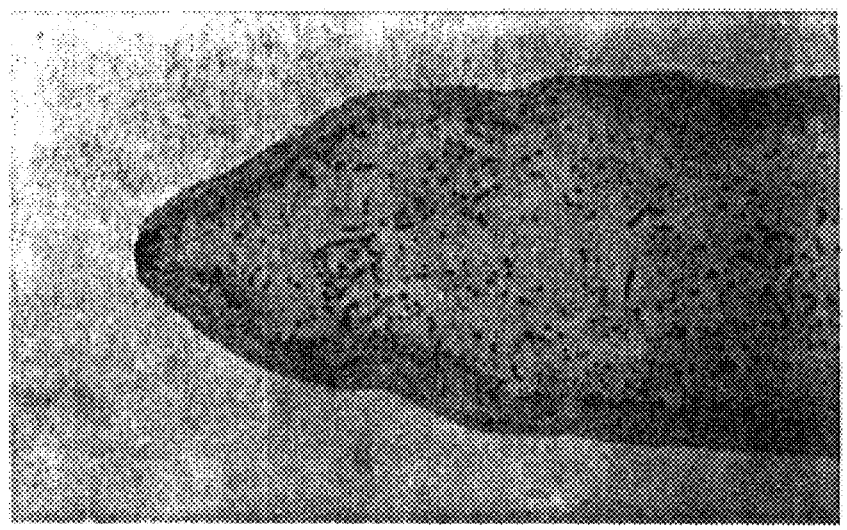

FIGS. 12A–12F: Immuno-histochemical staining of cartilage constructs. Samples were stained with normal rabbit serum (FIGS. 12A and 12B), anti-collaqen type I (FIGS. 12C and 12D), or anti-collagen type II (FIGS. 12E and 12F). Samples shown in FIGS. 12A, 12C, and 12E were grown without TGF-β while samples shown in FIGS. 12B, 12D and 12F were grown with TGF-β.

Figure 13A:
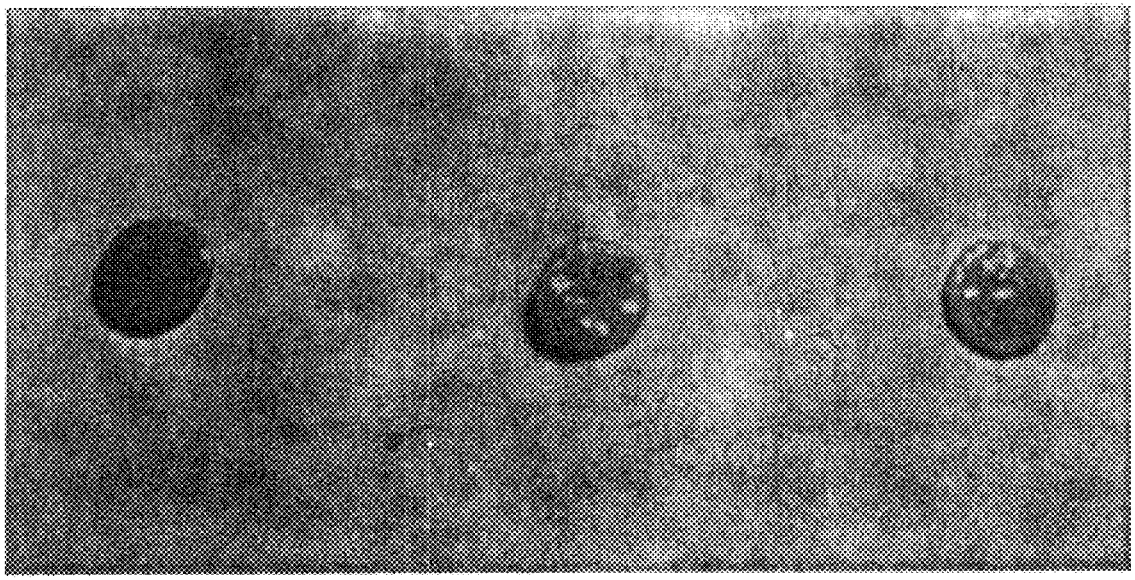
Figure 13B:
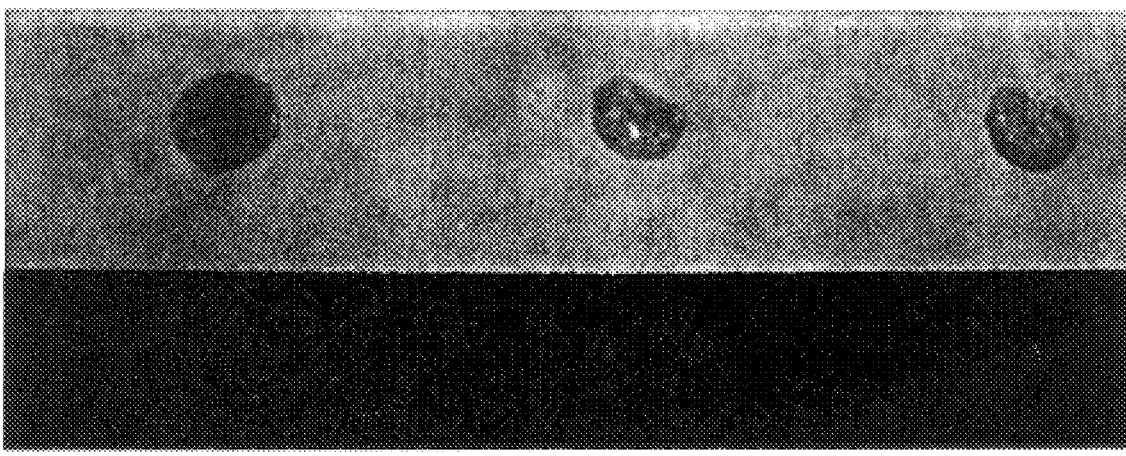

FIGS. 13A–13B: Cartilage-like tissue produced by bovine chondrocytes grown on PGA scaffolds. Bovine chondrocytes were seeded onto PGA scaffolds and grown for three weeks as described in Materials and Methods with (FIG. 13A) or without (FIG. 13B) TGF-β (20 ng/ml).

FIGS. 14A–14D: Hematoxylin and eosin staining of in vitro cartilage tissue. The samples were sectioned and stained with hematoxylin and eosin. Samples shown in FIGS. 14A and 14B were grown without TGF-β and samples shown in FIGS. 14C and 14D were grown with TGF-β.

Figure 15A:
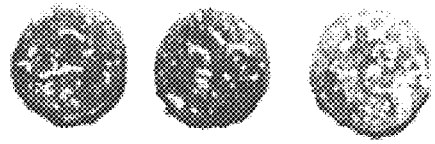
Figure 15A:
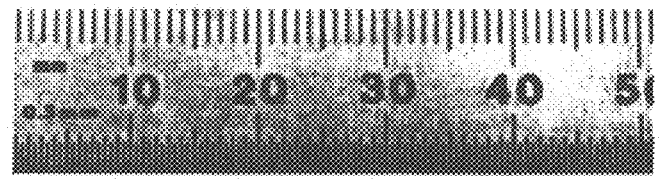
Figure 15B:
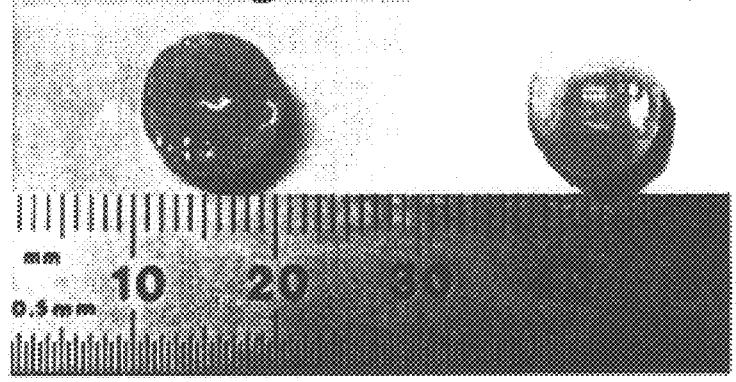

FIGS. 15A and 15B is a photograph of cartilage constructs (FIG. 15A) grown under static conditions and (FIG. 15B) grown in bioreactors.

Figure 16A:
Figure 16B:
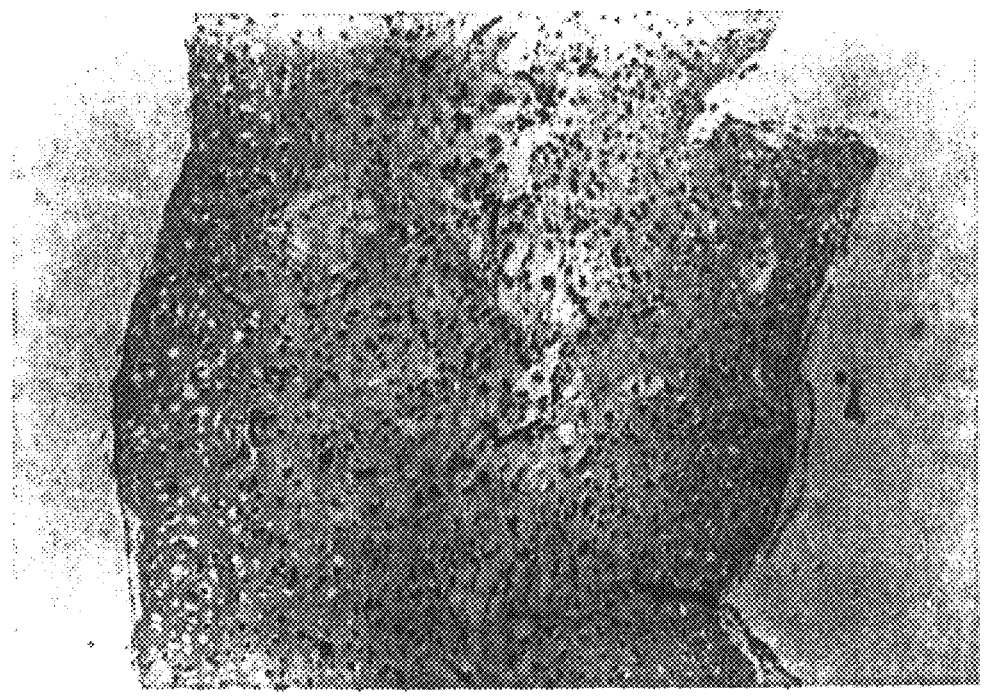
Figure 16C:
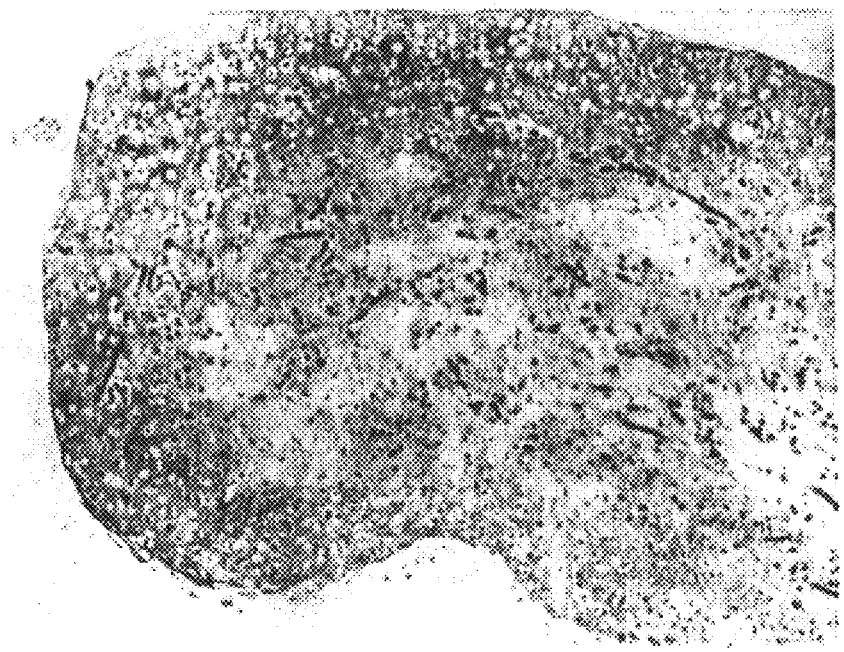
Figure 16D:
Figure 16E:
Figure 16F:
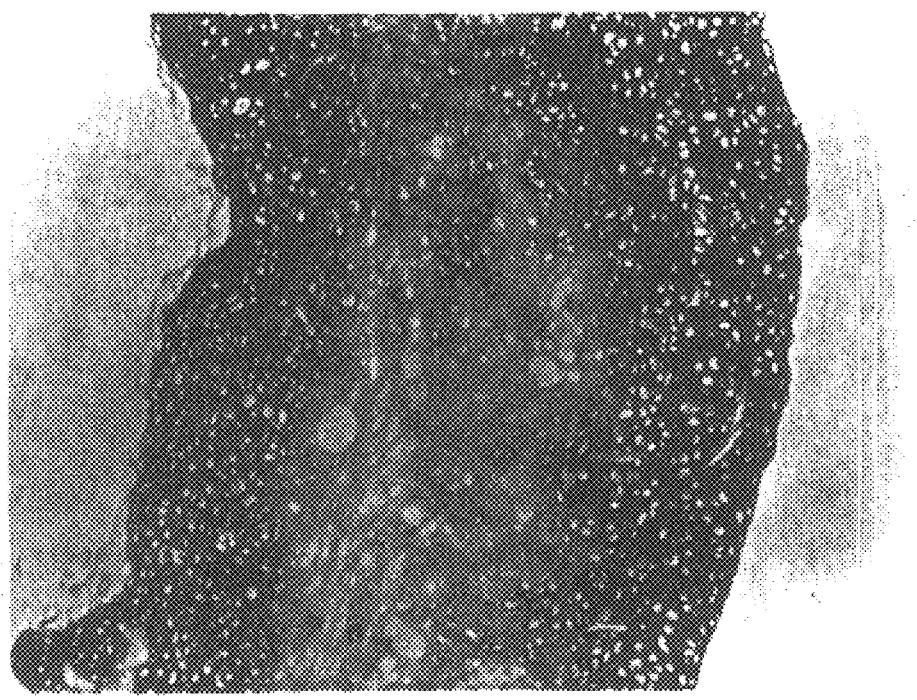
Figure 16G:
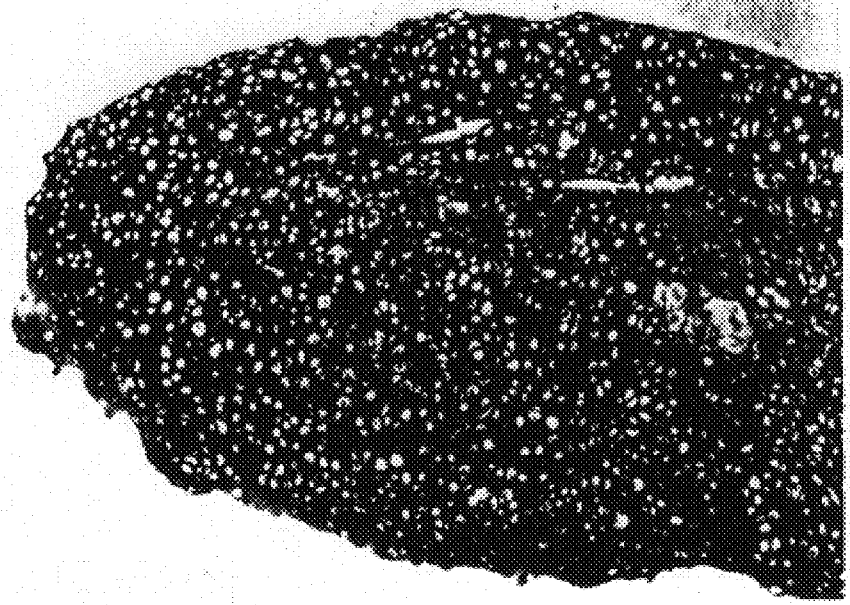
Figure 16H:
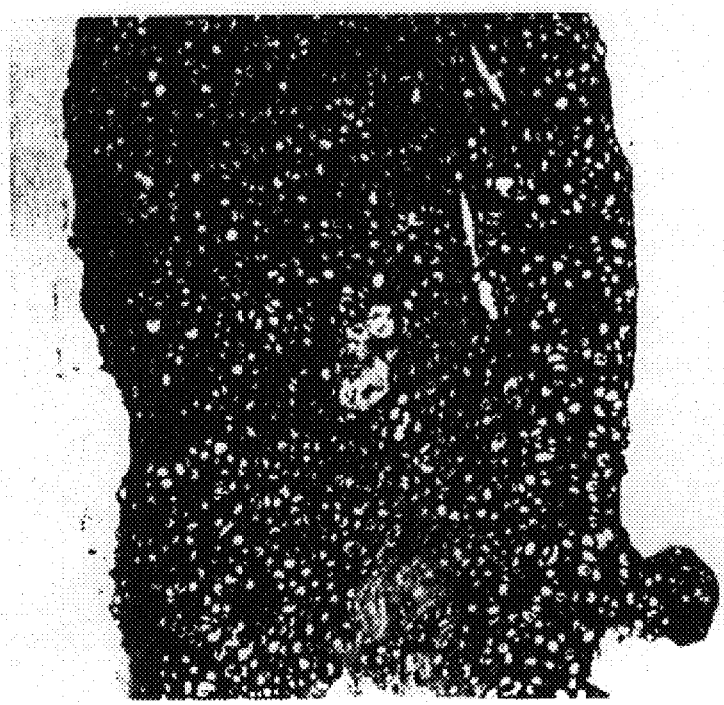
Figure 16:
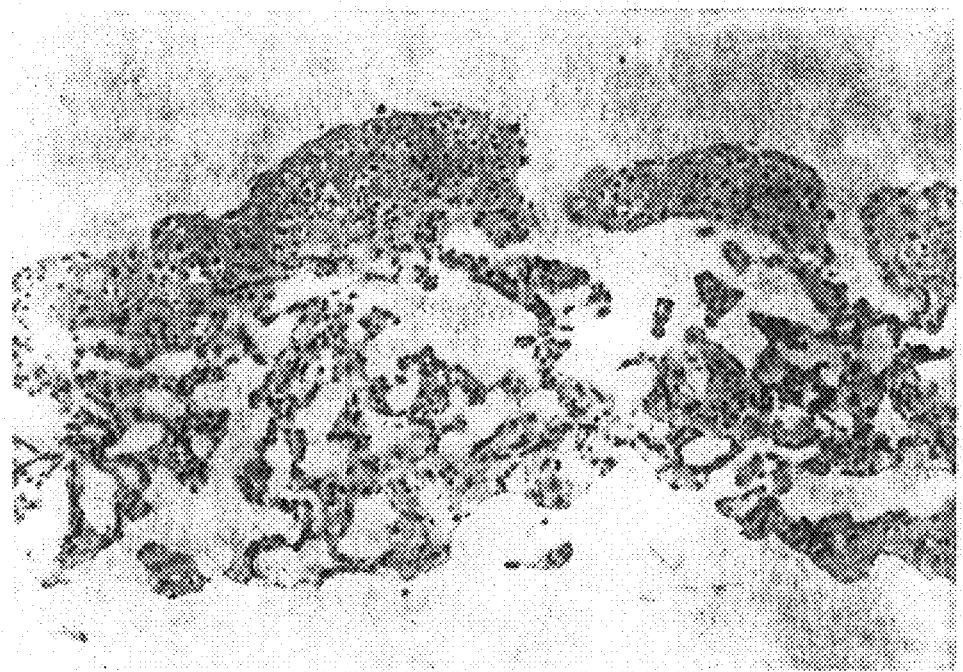
Figure 16J:

FIGS. 16A–16J describes cartilage produced in a bioreactor and stained with: FIGS. 16A and 16BL Hematoxylin-leosin; FIGS. 16C and 16D: Trichrome stain; 16E and 16F: Alcan Blue; and 16G and 16H: Safranin O. FIGS. 16I and 16J show hematoxylin/eosin and trichrome stain respectfully of a cartilage sample grown under static conditions.

Figure 17:
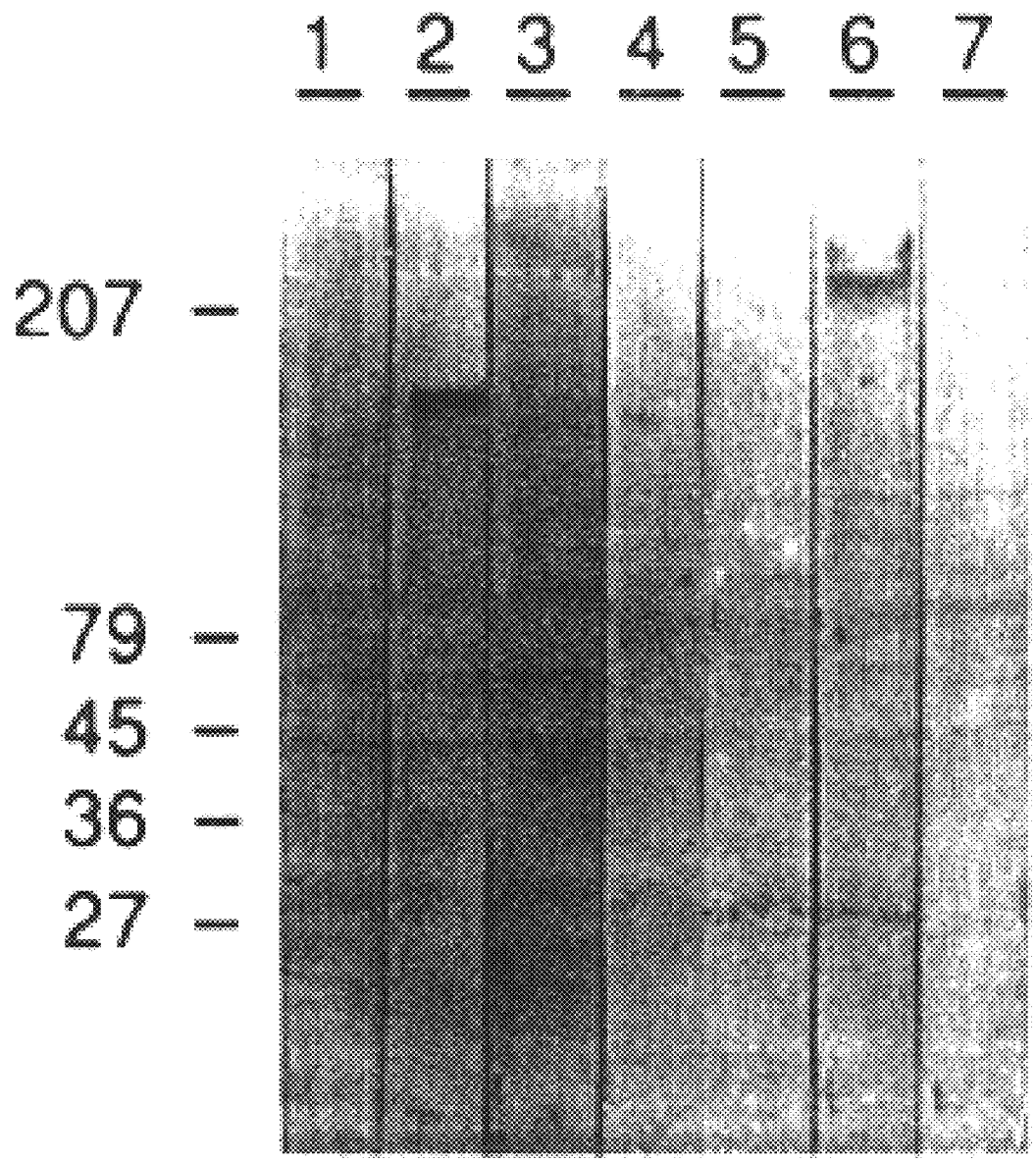

FIG. 17: Immunoblotting of bovine articular chondrocyte lysate. Cell lysates from bovine chondrocytes were examined by Western blotting using anti-type I collagen (lane 1), anti-type II collagen (lane 2), normal goat serum (lane 3), anti-versican (lane 4), normal rabbit serum (lane 5), anti-chondroitin sulfate (lane 6), normal mouse serum (lane 7).

Figure 18A:
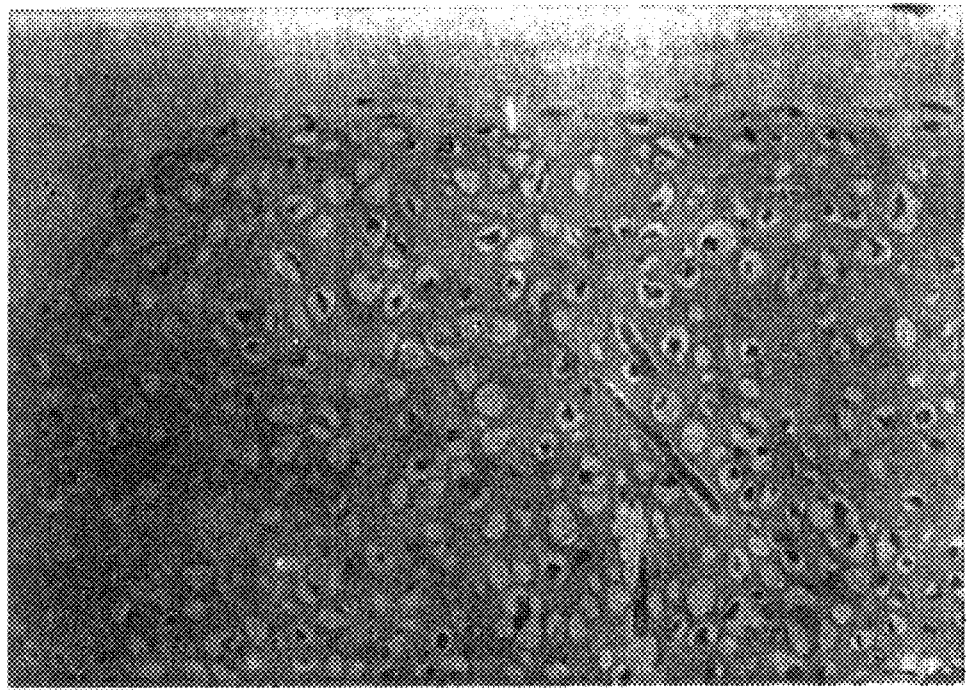
Figure 18B:
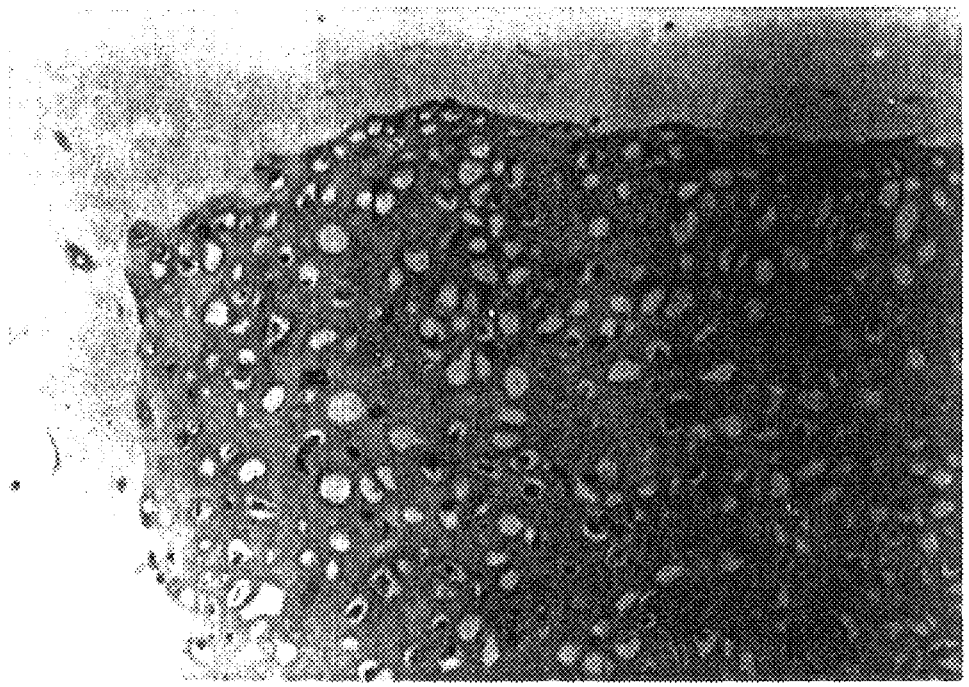
Figure 18C:
Figure 18D:
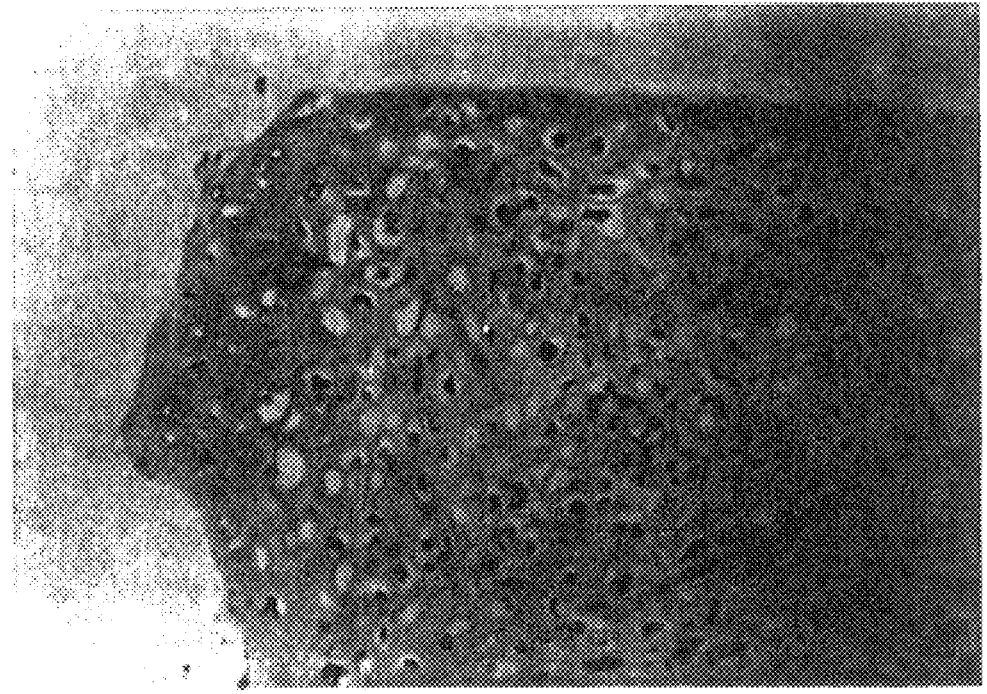

FIGS. 18A–18D: Immunohistochemical staining of cartilage constructs—cartilage constructs produced in a bioreactor was processed for immunohistochemical analysis and stained with: FIG. 18A antitype II collagen; FIG. 18B anti-chondroitin; FIG. 18C anti-type I collagen; and FIG. 18D normal rabbit serum.

5. DETAILED DESCRIPTION OF THE INVENTION: THE STIMULATION OF CELL PROLIFERATION AND APPROPRIATE CELL MATURATION

In accordance with the invention, stromal cells are inoculated onto a three-dimensional framework network or scaffold, and grown in culture to form a living cartilaginous material. The stromal cells may comprise chondrocytes, chondrocyte-progenitors, fibroblasts or fibroblast-like cells with or without additional cells and/or elements described more fully herein. The chondrocytes, fibroblast-like cells and other cells and/or elements that comprise the stroma may be fetal or adult in origin, and may be derived from convenient sources such as cartilage, skin, etc. Such tissues and/or organs can be obtained by appropriate biopsy or upon autopsy; cadaver organs may be used to provide a generous supply of stromal cells and elements. Alternatively, umbilical cord and placenta tissue or umbilical cord blood may serve as an advantageous source of fetal-type stromal cells, e.g., chondrocyte-progenitors and/or fibroblast-like cells for use in the three-dimensional system of the invention.

Fetal fibroblasts and/or chondrocytes can be inoculated onto the framework to form a "generic" living stromal tissue for culturing any of a variety of cells and tissues. However, in certain instances, it may be preferable to use a "specific" rather than "generic" stromal system, in which case stromal cells and elements can be obtained from a particular tissue, organ, or individual. For example, where the three-dimensional culture is to be used for purposes of transplantation or implantation in vivo, it may be preferable to obtain the stromal cells and elements from the individual who is to receive the transplant or implant. This approach might be especially advantageous where immunological rejection of the transplant and/or graft versus host disease is likely.

Once inoculated onto the three-dimensional matrix or framework, the stromal cells will proliferate on the framework and form the living stromal tissue which can be used in vivo. The three-dimensional living stromal tissue will sustain active proliferation of the culture for long periods of time. Because openings in the mesh permit the exit of stromal cells in culture, confluent stromal cultures do not exhibit contact inhibition, and the stromal cells continue to grow, divide, and remain functionally active.

The production of cartilage in the three-dimensional culture is improved by the application of intermittent pressurization and adequate supply of nutrients to stromal cells by convection.

Growth factors are not necessary since they are elaborated by the stromal support matrix. However, growth regulatory factors including, but not limited to, TGF-β and ascorbate, may be added to the culture. Because, according to the invention, it is important to recreate, in culture, the cellular microenvironment found in vivo for cartilage, the extent to which the stromal cells are grown prior to implantation in vivo or use in vitro may vary. In addition, the stromal cells grown in the system may be genetically engineered to produce gene products beneficial to transplantation, e.g. anti-inflammatory factors, e.g., anti-GM-CSF, anti-TNF, anti-IL-1, anti-IL-2, etc. Alternatively, the stromal cells may be genetically engineered to "knock out" expression of native gene products that promote inflammation, e.g., GM-CSF, TNF, IL-1, IL-2, or "knock out" expression of MHC in order to lower the risk of rejection. In addition, the stromal cells may be genetically engineered for use in gene therapy to adjust the level of gene activity in a patient to assist or improve the results of the cartilage transplantation.

The three-dimensional cultures may also be used in vitro for testing the effectiveness or cytotoxicity of pharmaceutical agents, and screening compounds.

In yet another application, the three-dimensional culture system may be used in a "bioreactor" to produce cartilage tissue constructs which possess critical biochemical, physical and structural properties of native human cartilage tissue by culturing the tissue under environmental conditions which are typically experienced by native cartilage tissue. The three-dimensional culture system may be maintained under intermittent and periodic pressurization and chondrocytes are provided an adequate supply of nutrients by convection. Pressure facilitates flow of fluid through the microporous three-dimensional cartilage construct, thereby improving the supply of nutrients and removal of waste from cells embedded in the construct.

Although the applicants are under no duty or obligation to explain the mechanism by which the invention works, a number of factors inherent in the three-dimensional culture system may contribute to its success:

(a) The three-dimensional matrix provides a greater surface area for protein attachment, and consequently, for the adherence of stromal cells.

(b) Because of the three-dimensionality of the matrix, stromal cells continue to actively grow, in contrast to cells in monolayer cultures, which grow to confluence, exhibit contact inhibition, and cease to grow and divide. The elaboration of growth and regulatory factors by replicating stromal cells may be partially responsible for stimulating proliferation and regulating differentiation of cells in culture.

(c) The three-dimensional matrix allows for a spatial distribution of cellular elements which is more analogous to that found in the counterpart tissue in vivo.

(d) The increase in potential volume for cell growth in the three-dimensional system may allow the establishment of localized microenvironments conducive to cellular maturation.

(e) The three-dimensional matrix maximizes cell—cell interactions by allowing greater potential for movement of migratory cells, such as macrophages, monocytes and possibly lymphocytes in the adherent layer.

(f) It has been recognized that maintenance of a differentiated cellular phenotype requires not only growth/differentiation factors but also the appropriate cellular interactions. The present invention effectively recreates the tissue microenvironment.

The three-dimensional stromal support, the culture system itself, and its maintenance, as well as various uses of the three-dimensional cultures are described in greater detail in the subsections below.

The three-dimensional chondrocyte cultures can be subjected to intermittent pressurization by creating elevated compressive forces through the plastic bag in which the cultures are housed by merely pinching or clamping the outlet valve. The chondrocytes respond to the ambient pressure at the level of cell division. There is an increase in the level of proteoglycans which accompanies increases in DNA synthesis.

The three-dimensional cartilage cultures of the invention are maintained in a bioreactor, a special device for creating intermittent and periodic pressurization and chondrocytes are provided an adequate supply of nutrients by convection. Maintaining an adequate supply of nutrients to chondrocyte cells throughout a replacement cartilage tissue construct of approximately 2–5 mm thickness is extremely important as the apparent density of the construct increases. The bioreactors may include a number of designs including, but not limited to, the "piston-style," hard plastic bioreactor; bellows; soft plastic bag with "pressure plate"; and soft plastic bag with "roller pins".

5.1. Establishment of Three-dimensional Stromal Tissue

The three-dimensional framework may be of any material and/or shape that: (a) allows cells to attach to it (or can be modified to allow cells to attach to it); and (b) allows cells to grow in more than one layer. A number of different materials may be used to form the matrix, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), nitrocellulose, cotton, polyglycolic acid (PGA), collagen (in the form of sponges, braids, or woven threads, etc.), cat gut sutures, cellulose, gelatin, or other naturally occurring biodegradable materials or synthetic materials, including, for example, a variety of polyhydroxyalkanoates. Any of these materials may be woven into a mesh, for example, to form the three-dimensional framework or scaffold. Certain materials, such as nylon, polystyrene, etc. are poor substrates for cellular attachment. When these materials are used as the three-dimensional framework, it is advisable to pre-treat the matrix prior to inoculation of stromal cells in order to enhance the attachment of stromal cells to the matrix. For example, prior to inoculation with stromal cells, nylon matrices could be treated with 0.1 M acetic acid and incubated in polylysine, PBS, and/or collagen to coat the nylon. Polystyrene could be similarly treated using sulfuric acid. Where the cultures are to be maintained for long periods of time or cryopreserved, non-degradable materials such as nylon, dacron, polystyrene, polyacrylates, polyvinyls, teflons, cotton, etc., may be preferred. A convenient nylon mesh which could be used in accordance with the invention is Nitex, a nylon filtration mesh having an average pore size of 210 μm and an average nylon fiber diameter of 90 μm (#3-210/36 Tetko, Inc., N.Y.).

Where the three-dimensional culture is itself to be implanted in vivo, it may be preferable to use biodegradable matrices such as polyglycolic acid, catgut suture material, collagen, or gelatin, for example. The polyglycolic acid is commonly sterilized in preparation for long-term in vitro, with ethylene oxide or by irradiating with an electron beam. Unfortunately, both these procedures have deleterious effects on the cells growing on the three-dimensional culture matrices. For example, ethylene oxide is toxic to the cells in culture and therefore, electron beam treatment is preferred. However, treatment with the electron beam results in cells falling off the framework before depositing adequate extracellular matrix. The addition of TGF-β to the cultured cells overcomes this problem.

Stromal cells comprising chondrocytes chondrocyte-progenitors, fibroblasts or fibroblast-like cells, with or without other stromal cells and elements described below, are inoculated onto the framework. Growth factors, such as TGF-β may be added to the culture prior to, during or subsequent to inoculation of the stromal cells. The concentration of TGF-β maintained in the cultures can be monitored and adjusted to optimize growth. Alternatively, host cells that are genetically engineered to express and produce TGF-β may be included in the inoculum; such cells can include genetically engineered stromal cells. These cells would serve as a source of TGF-β or other protein factor(s) in the culture. Preferably, the gene or coding sequence for TGF-β would be placed under the control of a regulated promoter, so that production of TGF-β in culture can be controlled. The genetically engineered cells will be screened to select those cell types: 1) that bring about the amelioration of symptoms of rheumatoid disease or inflammatory reactions in vivo, and 2) escape immunological surveillance and rejection.

Stromal cells such as chondrocytes may be derived from articular cartilage, costal cartilage, etc. which can be obtained by biopsy (where appropriate) or upon autopsy. Fibroblasts can be obtained in quantity rather conveniently from foreskin or, alternatively, any appropriate cadaver organ. Fetal cells, including fibroblast-like cells, chondrocyte-progenitors, may be obtained from umbilical cord or placenta tissue or umbilical cord blood. Such fetal stromal cells can be used to prepare a "generic" stromal or cartilaginous tissue. However, a "specific" stromal tissue may be prepared by inoculating the three-dimensional matrix with fibroblasts derived a particular individual who is later to receive the cells and/or tissues grown in culture in accordance with the three-dimensional system of the invention.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, Dnase, pronase, etc. Mechanical disruption can also be accomplished by a number of methods including, but not limited to the use of grinders, blenders, sieves, homogenizers, pressure cells, or sonicators to name but a few. For a review of tissue disaggregation techniques, see Freshney, Culture of Animal Cells. A Manual of Basic Technique, 2d Ed., A. R. Liss, Inc., New York, 1987, Ch. 9, pp. 107–126.

Fibroblast-like cells may also be isolated from human umbilical cords (33–44 weeks). Fresh tissues may be minced into pieces and washed with medium or snap-frozen in liquid nitrogen until further use. The umbilical tissues may be disaggregated as described above.

Once the tissue has been reduced to a suspension of individual cells, the suspension can be fractionated into subpopulations from which the fibroblasts and/or other stromal cells and/or elements can be obtained. This also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, counter current distribution, electrophoresis and fluorescence-activated cell sorting. For a review or clonal selection and cell separation techniques, see Freshney, Culture of Animal Cells. A Manual of basic Techniques, 2d Ed., A. R. Liss, Inc., New York, 1987, Ch. 11 and 12, pp. 137–168.

The isolation of chondrocytes, chondrocyte-progenitors, fibroblasts or fibroblast-like cells may, for example, be carried out as follows: fresh tissue samples are thoroughly washed and minced in Hanks balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated stromal cells can then be grown to confluency, lifted from the confluent culture and inoculated onto the three-dimensional support (see, Naughton et al., 1987, J. Med. 18 (3 &4):219–250). Inoculation of the three-dimensional matrix with a high concentration of stromal cells, e.g., approximately $10^6$ to $5 \times 10^7$ cells/ml, will result in the establishment of the three-dimensional stromal support in shorter periods of time.

In addition to chondrocytes, chondrocyte-progenitors, fibroblasts or fibroblast-like cells, other calls may be added to form the three-dimensional stromal tissue required to support long term growth in culture. For example, other cells found in loose connective tissue may be inoculated onto the three-dimensional support along with chondrocytes or fibroblasts. Such cells include but are not limited to endothelial cells, pericytes, macrophages, monocytes, plasma cells, mast cells, adipocytes, etc. These stromal cells may readily be derived from appropriate organs including umbilical cord or placenta or umbilical cord blood using methods known in the art such as those discussed above.

Again, where the cultured cells are to be used for transplantation or implantation in vivo it is preferable to obtain the stromal cells from the patient's own tissues. The growth of cells on the three-dimensional support may be further enhanced by adding to the framework or coating the framework with proteins (e.g., collagens, elastic fibers, reticular fibers) glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials.

After inoculation of the stromal cells, the three-dimensional matrix should be incubated in an appropriate nutrient medium. Many commercially available media such as DMEM, RPMI 1640. Fisher's Iscove's, McCoy's, and the like may be suitable for use. It is important that the three-dimensional stromal matrix be suspended or floated in the medium during the incubation period in order to maximize proliferative activity. In addition, the culture should be "fed" periodically to remove the spent media, depopulate released cells, and add fresh media. The concentration of TGF-β may be adjusted during these steps. In chondrocyte cultures, proline, a non-essential amino acid and ascorbate are also included in the cultures.

These procedures are greatly facilitated when carried out using a bioreactor, which is a closed system housing the three-dimensional framework inoculated with stromal cells. A bioreactor reduces the possibility of contamination, maintains the cultures under intermittent and periodic pressurization to create environmental conditions that maintain an adequate supply of nutrients to chondrocyte cells throughout the cartilage tissue construct by convection.

During the incubation period, the stromal cells will grow linearly along and envelop and colonize the three-dimensional matrix before beginning to grow into the openings of the matrix. It is important to grow the cells to an appropriate degree which reflects the amount of stromal cells present in the in vivo tissue prior to inoculation of the stromal tissue with the tissue-specific cells.

The openings of the framework should be of an appropriate size to allow the stromal cells to stretch across the openings. Maintaining actively growing stromal cells which stretch across the framework enhances the production of growth factors which are elaborated by the stromal cells, and hence will support long term cultures. For example, if the openings are too small, the stromal cells may rapidly achieve confluence but be unable to easily exit from the mesh; trapped cells may exhibit contact inhibition and cease production of the appropriate factors necessary to support proliferation and maintain long term cultures. If the openings are too large, the stromal cells may be unable to stretch across the opening; this will also decrease stromal cell production of the appropriate factors necessary to support proliferation and maintain long term cultures. When using a mesh type of matrix, as exemplified herein we have found that openings ranging from abut 150 µm to about 220 µm will work satisfactory. However, depending upon the three-dimensional structure and intricacy of the framework, other sizes may work equally well. In fact, any shape or structure that allow the stromal cells to stretch and continue to replicate and grow for lengthy time periods will work in accordance with the invention.

Different proportions of the various types of collagen deposited on the framework can affect the growth of later inoculated tissue-specific parenchymal cells. For three-dimensional skin culture systems, collagen types I and III are preferably deposited in the initial matrix. The proportions of collagen types deposited can be manipulated or enhanced by selecting fibroblasts which elaborate the appropriate collagen type. This can be accomplished using monoclonal antibodies of an appropriate isotypes or subclass that is capable of activating complement, and which define particular collagen type. These antibodies and complement can be used to negatively select the fibroblasts which express the desired collagen type. Alternatively, the stroma used to inoculate the matrix can be a mixture of cells which synthesize the appropriate collagen types desired. The distribution and origins of the five types of collagen is shown in Table I.

TABLE I

DISTRIBUTIONS AND ORIGINS OF
THE FIVE TYPES OF COLLAGEN

| Collagen | Principal Tissue Distribution | Cells of origin |
|---|---|---|
| | connective tissue; collagen fibers | reticular cells; smooth muscle cells |
| | Fibrocartilage Bone Dentin | Osteoblast Odontoblasts |
| II | Hyaline and elastic cartilage | Chondrocytes |
| | Vitreous body of eye | Retinal cells |
| III | Loose connective tissue; reticular fibers Papillary layer of dermis | Fibroblasts and reticular cells |
| | Blood vessels | Smooth muscle cells; endothelial cells |
| IV | Basement membranes | Epithelial and endothelial cells |
| | Lens capsule of eye | Lens fibers |
| V | Fetal membranes; placenta Basement membranes Bone | Fibroblast |
| | Smooth muscle | Smooth muscle cells |

Thus, depending upon the tissue to be cultured and the collagen types desired, the appropriate stromal cell(s) may be selected to inoculate the three-dimensional matrix. For example, for the growth and preparation of cartilage, chondrocytes, chondrocyte-progenitors, fibroblasts or fibroblast-like cells should be used.

During incubation of the three-dimensional stromal support, proliferating cells may be released from the matrix. These released cells may stick to the walls of the culture vessel where they may continue to proliferate and form a confluent monolayer. This should be prevented or minimized, for example, by removal of the released cells during feeding, or by transferring the three-dimensional stromal matrix to a new culture vessel. The presence of a confluent monolayer in the vessel will "shut down" the growth of cells in the three-dimensional matrix and/or culture. Removal of the confluent monolayer or transfer of the matrix to fresh media in a new vessel will restore proliferative activity of the three-dimensional culture system. Such removal or transfers should be done in any culture vessel which has a stromal monolayer exceeding 25% confluency. Alternatively, the culture system could be agitated to prevent the released cells from sticking, or instead of periodically feeding the cultures, the culture system could be set up so that fresh media continuously flows through the system by convection. The flow rate could be adjusted to both maximize proliferation within the three-dimensional culture, and to wash out and remove cells released from the matrix, so that they will not stick to the walls of the vessel and grow to confluence. In any case, the released stromal cells can be collected and cryopreserved for future use.

5.2. Uses of the Three-Dimensional Culture System

The three-dimensional culture system of the invention can be used in a variety of applications. These include but are not limited to transplantation or implantation of either the cultured cells obtained from the matrix, or the cultured matrix itself in vivo; screening the effectiveness and cytotoxicity of compounds, allergens, growth/regulatory factors, pharmaceutical compounds, etc., in vitro; elucidating the mechanism of certain diseases; studying the mechanism by which drugs and/or growth factors operate; diagnosing and monitoring cancer in a patient; gene therapy; and the production of biologically active products, to name but a few.

5.2.1. Transplantation In Vivo

The biological replacement cartilage tissue constructs produced in the three-dimensional culture system of the invention can be used to replace or augment existing cartilage tissue, to introduce new or altered tissue, to modify artificial prostheses, or to join biological tissues or structures. For example, and not by way of limitation, specific embodiments of the invention would include i) hip prostheses coated with replacement cartilage tissue constructs grown in three-dimensional cultures; ii) knee reconstruction with cartilage tissue constructs; and iii) prostheses of other joints requiring reconstruction and/or replacement of articular cartilage.

The evaluation of internal derangements of articular cartilage in several articulations, including the knee, hip, elbow, ankle and the glenohumeral joint, has been made possible by arthroscopic techniques. Arthroscopic surgery has become increasingly popular as well as successful, e.g., numerous small cutting tools, 3 to 4 mm in diameter can be used in the knee. Triangulation, in which the operating instruments are brought into the visual field provided by the arthroscope, requires multiple portals of entry; alternatively, the cutting tools can be passed through a channel in the arthroscope itself in which case only one opening in the joint is necessary (Jackson, R. W., 1983, J. Bone Joint Surg. [AM] 65:416. Selective removal of the injured or deteriorated portion with arthroscopic surgery, followed by cartilage grafting can be employed successfully. Cartilage tissue constructs can also be employed in major reconstructive surgery for different types of joints. Detailed procedures have been described in Resnick, D., and Niwayama, G., eds., 1988, *Diagnosis of Bone and Joint Disorders*, 2d ed., W. B. Sanders Co.

Three-dimensional tissue culture implants may, according to the inventions, be used to replace or augment existing tissue, to introduce new or altered tissue, or to join together biological tissues or structures.

5.2.2. Screening Effectiveness and Cytotoxicity of Compounds In Vitro

The three-dimensional cultures may be used in vitro to screen a wide variety of compounds, for effectiveness and cytotoxicity of pharmaceutical agents, growth/regulatory factors, anti-inflammatory agents, etc. To this end, the cultures are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the three-dimensional system may be assessed.

The three-dimensional cultures of the invention may be used as model systems for the study of physiologic or pathologic conditions. For example, joints that are immobilized suffer relatively quickly in a number of respects. The metabolic activity of chondrocytes appears affected, as loss of proteoglycans and an increase in water content are soon observed. The normal white, glistening appearance of the cartilage changes to a dull, bluish color, and the cartilage thickness is reduced. However, how much of this process is due to nutritional deficiency and how much is due to upset in the stress-dependent metabolic homeostasis is not yet clear. The three-dimensional chondrocyte culture system may be used to determine the nutritional requirements of cartilage under different physical conditions, e.g., intermittent pressurization and by pumping action of nutrient medium into and out of the cartilage construct. This may be especially useful in studying underlying causes for age-related, or injury-related decrease in tensile strength of articular cartilage, e.g., in the knee, that predisposes the weakened cartilage to traumatic damage.

According to the present invention, the three-dimensional chondrocyte cultures may also be used to study the mechanism of action of cytokines and other pro-inflammatory mediators released in rheumatic disease in the synovial fluid, e.g., IL-1, TNF and prostaglandins. The patient's own joint fluid could be used in vitro to study the effect of these compounds on chondrocyte growth and to screen cytotoxic and/or pharmaceutical agents that are most efficacious for a particular patient; i.e., those that prevent resorption of cartilage and enhance the balanced growth of articular cartilage. Those agents could then be used to therapeutically treat the patient.

5.2.3. Genetically Engineered Cartilage

The three-dimensional culture system of the invention may afford a vehicle for introducing genes and gene products in vivo to assist or improve the results of the transplantation and/or for use in gene therapies. For example, the stromal cells can be genetically engineered to express anti-inflammatory gene products to reduce the risk of failure or degenerative changes in the cartilage due to rheumatoid disease of inflammatory reactions. In this regard, the stromal cells can be genetically engineered to express anti-inflammatory gene products, for example, peptides or polypeptides corresponding to the idiotype of neutralizing antibodies for granulocyte-macrophage colony stimulating factor (GM-CSF), TNF, IL-1, IL-2, or other inflammatory cytokines. Il-1 has been shown to decrease the synthesis of proteoglycans and collagens type II, IX, and XI (Tyler et al., 1985, Biochem. J. 227:869–878; Tyler et al., 1988, Coll. Relat. Res. 82:393–405; Goldring et al., 1988, J. Clin. Invest. 82:2026–2037; and Lefebvre et al., 1990, Biophys. Acta. 1052:366–372. TNF also inhibits synthesis of proteoglycans and type II collagen although it is much less potent than IL-1 (Yaron, I., et al., 1989, Arthritis Rheum. 32:173–180; Ikebe, T., et al., 1988, J. Immunol. 140:827–831; and Saklatvala, J., 1986, Nature 322:547–549.

Preferably, the cells are engineered to express such gene products transiently and/or under inducible control during the post-operative recovery period, or as a chimeric fusion protein anchored to the stromal cells, for example, a chimeric molecule composed of an intracellular and/or transmembrane domain of a receptor or receptor-like molecule, fused to the gene product as the extracellular domain. In another embodiment, the stromal cells could be genetically engineered to express a gene for which a patient is deficient, or which would exert a therapeutic effect, e.g., TGF-$\beta$ to stimulate cartilage production, etc. The genes of interest engineered into the stromal cells need to be related to rheumatoid or joint disease.

The stromal cells can be engineered using a recombinant DNA construct containing the gene used to transform or transfect a host cell which is cloned and then clonally expanded in the three-dimensional culture system. The three-dimensional culture which expresses the active gene product, could be implanted into an individual who is deficient for that product. For example, genes that prevent or ameliorate symptoms of various types of rheumatoid or joint diseases may be underexpressed or down regulated under disease conditions. Specifically, expression of genes involved in preventing inflammatory reactions in rheumatoid or joint diseases may be down-regulated. Alternatively, the activity of gene products may be diminished, leading to the manifestations of some or all of the above pathological conditions and eventual development of symptoms of rheumatoid or joint diseases. Thus, the level of gene activity may be increased by either increasing the level of gene product present or by increasing the level of the active gene product which is present in the three-dimensional culture system. The three-dimensional culture which expresses the active target gene product can then be implanted into the rheumatoid or joint disease patient who is deficient for that product. "Target gene," as used herein, refers to a gene involved in rheumatoid or joint diseases in a manner by which modulation of the level of target gene expression or of target gene product activity may act to ameliorate symptoms of rheumatoid or joint diseases by preventing resorption of cartilage and production of inflammatory mediators by chondrocytes.

Further, patients may be treated by gene replacement therapy during the post-recovery period after cartilage transplantation. Replacement cartilage tissue constructs or sheets may be designed specifically to meet the requirements of an individual patient, for example, the stromal cells may be genetically engineered to regulate one or more genes; or the regulation of gene expression may be transient or long-term; or the gene activity may be non-inducible or inducible. For example, one or more copies of a normal target gene, or a portion of the gene that directs the production of a normal target gene protein product with target gene function, may be inserted into human cells that populate the three-dimensional constructs using either non-inducible vectors including, but are not limited to, adenovirus, adeno-associated virus, and retrovirus vectors, or inducible promoters, including metallothionien, or heat shock protein, in addition to other particles that introduce DNA into cells, such as liposomes or direct DNA injection or in gold particles. For example, the gene encoding the human complement regulatory protein, which prevents rejection of the graft by the host, may be inserted into human fibroblasts. McCurry et al., 1995, Nature Medicine 1:423–427.

The three-dimensional cultures containing such genetically engineered stromal cells, e.g., either mixtures of stromal cells each expressing a different desired gene product, or a stromal cell engineered to express several specific genes are then implanted into the patient to allow for the amelioration of the symptoms of rheumatoid or joint disease. The gene expression may be under the control of a non-inducible (i.e., constitutive) or inducible promoter. The level of gene expression and the type of gene regulated can be controlled depending upon the treatment modality being followed for an individual patient.

The use of the three-dimensional culture in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the three-dimensional cultures of the invention allow for expansion of the number of transfected cells and amplification (via cell division) of transfected cells.

A variety of methods may be used to obtain the constitutive or transient expression of gene products engineered into the stromal cells. For example, the transkaryotic implantation technique described by Seldon et al., 1987, Science 236:714–718 can be used. "Transkaryotic", as used herein, suggests that the nuclei of the implanted cells have been altered by the addition of DNA sequences by stable or transient transfection. The cells can be engineered using any of the variety of vectors including, but not limited to, integrating viral vectors, e.g., retrovirus vector or adeno-associated viral vectors, or non-integrating replicating vectors, e.g., papilloma virus vectors, SV40 vectors, adenoviral vectors; or replication-defective viral vectors. Where transient expression is desired, non-integrating vectors and replication defective vectors may be preferred, since either inducible or constitutive promoters can be used in these systems to control expression of the gene of interest. Alternatively, integrating vectors can be used to obtain transient expression, provided the gene of interest is controlled by an inducible promoter.

Preferably, the expression control elements used should allow for the regulated expression of the gene so that the product is synthesized only when needed in vivo. The promoter chosen would depend, in part upon the type of tissue and cells cultured. Cells and tissues which are capable of secreting proteins (e.g., those characterized by abundant rough endoplasmic reticulum, and golgi complex) are preferable. Hosts cells can be transformed with DNA controlled by appropriate expression control elements (e.g., promoter, enhancer, sequences, transcription terminators, polyadenylation sites, etc.) and a selectable marker. Following the introduction of the foreign DNA, engineered cells may be allowed to grow in an enriched media, and then are switched to a selective media. The selectable marker in the recombinant plasmid confers resistance to the selection and allows cells to stably integrate the plasmid into their chromosomes and grow to form foci which, in turn, can be cloned and expanded into cell lines. This method can advantageously be used to engineer cell lines which express the gene protein product.

Any promoter may be used to drive the expression of the inserted gene. For example, viral promoters include but are not limited to the CMV promoter/enhancer, SV 40, papillomavirus, Epstein-Barr virus, elastin gene promoter and β-globin. If transient expression is desired, such constitutive promoters are preferably used in a non-integrating and/or replication-defective vector. Alternatively, inducible promoters could be used to drive the expression of the inserted gene when necessary. For example, inducible promoters include, but are not limited to, metallothionien and heat shock protein.

Examples of transcriptional control regions that exhibit tissue specificity which have been described and could be used, include but are not limited to: elastase I gene control region which is active in pancreatic acinar cells (Swit et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122); immunoglobulin gene control region which is active in lymphoid cells (Grosschedl et al., 1984, Cell 3S:647–658: Adams et al., 1985, Nature 318:533–538; Alexander et al., 1987, Mol. Cell. Biol. 7:1436–1444); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286); and gonadotropic releasing hormone gene control region which is active in the hypothalamus (Mason et al., 1986, Science 234:1372–1378).

Once genetically engineered cells are implanted into an individual, the presence of the anti-inflammatory gene products, for example, peptides or polypeptides corresponding to the idiotype of neutralizing antibodies for GM-CSF, TNF, IL-1, IL-2, or other inflammatory cytokines, can bring about amelioration of the inflammatory reactions associated with rheumatoid or joint disease. IL-1 is a potent stimulator or cartilage resorption and of the production of inflammatory mediators by chondrocytes (Campbell et al., 1991, J. Immun. 147:1238–1246).

The stromal cells used in the three-dimensional culture system of the invention may be genetically engineered to "knock out" expression of factors that promote inflammation or rejection at the implant site. Negative modulatory techniques for the reduction of target gene expression levels or target gene product activity levels are discussed below. "Negative modulation", as used herein, refers to a reduction in the level and/or activity of target gene product relative to the level and/or activity of the target gene product in the absence of the modulatory treatment. The expression of a gene native to stromal cell can be reduced or knocked out using a number of techniques, for example, expression may be inhibited by inactivating the gene completely (commonly termed "knockout") using the homologous recombination technique. Usually, an exon encoding an important region of the protein (or an exon 5' to that region) is interrupted by a positive selectable marker (for example neo), preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted. Mombaerts et al., 1991, Proc. Nat. Acad. Sci. U.S.A. 88:3084–3087.

Antisense and ribozyme molecules which inhibit expression of the target gene can also be used in accordance with the invention to reduce the level of target gene activity. For example, antisense RNA molecules which inhibit the expression of major histocompatibility gene complexes (HLA) shown to be most versatile with respect to immune responses. Still further, triple helix molecules can be utilized in reducing the level of target gene activity. These techniques are described in detail by L. G. Davis et al., eds, *Basic Methods in Molecular Biology,* 2nd ed., Appleton & Lange, Norwalk, Conn. 1994.

Using any of the foregoing techniques, the expression of IL-1 can be knocked out in the chondrocytes to reduce the risk of resorption of cartilage and production of inflammatory mediators by the chondrocytes. Likewise, the expression of MHC class II molecules can be knocked out in order to reduce the risk of rejection of the graft.

In yet another embodiment of the invention, the three-dimensional culture system could be used in vitro to produce biological products in high yield. For example, a cell which naturally produces large quantities of a particular biological product (e.g., a growth factor, regulatory factor, peptide hormone, antibody, etc.), or a host cell genetically engineered to produce a foreign gene product, could be clonally expanded using the three-dimensional culture system in vitro. If the transformed cell excretes the gene product into the nutrient medium, the product may be readily isolated from the spent or conditioned medium using standard separation techniques (e.g., HPLC, column chromatography, electrophoretic techniques, to name but a few). A "bioreactor" has been devised which takes advantage of the flow method for feeding the three-dimensional cultures in vitro. Essentially, as fresh media is passed through the three-dimensional culture, the gene product is washed out of the culture along with the cells released from the culture. The gene product is isolated (e.g., by HPLC column chromatography, electrophoresis, etc.) from the outflow of spent or conditioned media. The bioreactor system is specially designed to allow for pressurization of the chamber during growth of the cartilage tissue and supply nutrients to stromal cells by convection.

6. EXAMPLE: THREE-DIMENSIONAL CHONDROCYTE CULTURE SYSTEM

The three-dimensional culture of the present invention provides for the replication and colonization of chondrocytes in vitro, in a system comparable to physiologic conditions. Importantly, the chondrocyte cells replicated in this system include all of the cells present in normal cartilage tissue, assuming all cell types were present in the original chondrocyte inoculum used to initiate the cultures. Cartilage implants can be of one or more types of cartilage, depending primarily on the location of the implant and the type of cartilage cells seeded onto the polymeric matrix. The following examples describe: (i) a method of growing rabbit chondrocytes seeded on a biodegradable polyglycolic acid matrix sterilized by ethylene oxide or electron beam with or without TGF-β; (ii) a method of growing bovine chondrocytes on a polyglycolic acid matrix in a culture containing TGF-β with or without ascorbate; and iii) a method of growing rabbit chondrocytes on a polyglycolic acid matrix placed in a bioreactor. Specific conditions used are described below.

6.1. Material and Methods

6.1.1. Growth Factors

Recombinant TGF-$β_1$ prepared according to Gentry et al., 1987, Mol. Cell. Biol. 7:3418–3427, was used at the concentration of 20 ng/ml. Recombinant human beta fibroblast growth factor (βFGF), Pepro Tech., Inc., Rocky Hill, N.J., was used at the concentration of 10 mg/ml. Ascorbic acid or ascorbate was used at the concentration of 50 μg/ml.

6.1.2. Cells

Cartilage was harvested from articular surfaces of healthy mature (2–3 years old) cows or New Zealand white rabbits (4–8 months old). The cartilage pieces were digested with collagenase (0.2% weight/volume) in complete media DMEM containing 10% fetal bovine serum, 2 mM L-glutamine, non-essential amino acids, 50 mg/ml proline, 1 mM sodium pyruvate and 35 μg/ml gentamicin for 20 hr. at 37° C. Liberated chondrocytes were spun, resuspended in complete medium, counted and plated at $10^6$ cells per T-150 flask. Cells were routinely passed at confluence (every 5–7 days).

6.1.3. Cell Seeding

Polyglycolic acid mesh (45 mg/cc; non-heat plated; 2 mm thick; 1 cm diameter) was sterilized by ethylene oxide or electron beam (E-beam, 3MR) treatment and presoaked overnight in complete medium. The mesh was seeded in 6-well dishes with 3–4×$10^6$ cells per mesh for 2 days at 37° C. in complete medium and placed in an incubator or bioreactor depending on the protocol used. Medium containing ascorbate was changed two–three times per week. Samples were then washed with PBS and processed for histology after a specific period of growth.

6.1.4. Histology and Immunohistochemistry

Tissues were washed in PBS at harvesting and photographed. They were fixed in 10% buffered formalin, paraffin embedded and stained with hematoxylin and eosin (H&E) and/or trichrome and/or Safranin O. For some samples, immunohistochemical staining was also performed on paraffin embedded tissue using Biotin-Streptavidin Amplified System (Biogenex Corp.) to unmask antigenic sites. They were then incubated with 3% hydrogen peroxide to block endogenous peroxidase activity, rinsed with tris-saline buffer and incubated with biotin block serum (Dako, Inc.) to reduce nonspecific background. Blocking serum was tapped off and primary antibodies to collagen type I and collagen type II were added. Sections were then incubated with biotinlated anti-lgG, and washed with tris-saline buffer. They were then incubated with horseradish peroxidase-conjugated streptavidin and washed with tris-saline. Sections were then incubated with 3,3-diaminobenzidine substrate and counterstained with hematoxylin.

6.1.5. Immunoblotting

Confluent monolayers of articular chondrocytes were scraped in PBS containing 1% Tween 20. Lupis buffer (as described in Laemmli, U. K., 1970, Nature 227:680–685) was added and cell lysates were fractionated by SDS-PAGE and by immunoblotting as described in Burnette, W. N., 1981, Anal. Chem. 112:195–203. Antibodies to collagen type I and II were obtained from Southern Biochemicals, Inc. (Birmingham, Ala.) and anti-chondroitin sulfate antibody was from Sigma (St. Louis, Mo.).

6.1.6. Quantitation of Collagen and GAG

Constructs were frozen lyophilized and stored at −70° C. until analysis. The constructs were digested with papain (1 mg/ml) in 100 mM phosphate buffer (pH 6.5) containing 5 mM cysteine and 5 mm EDTA at 65° C. overnight. Quantitation of collagen and GAG were determined according to the methods described (Farndale et al., 1986, Biochem. Biophys. Acta 883:73–177; Woessner, J. F., 1961, Archiv. Biochem. Biophys. 93:440–447.

6.1.7. Northern Blot Analysis

RNA was isolated, fractionated on agarose-formaldehyde gels and probed with [$^{32}$P]-labelled type II collagen cDNA as described (Chomczynski, P., and Sacchi, N., 1987, Anal. Biochem. 162; Lehrach et al., 1977, Biochemistry 16:4743–4751; and Madisen et al., 1986, DNA 7:1–8).

6.2. Effect of Ethylene Oxide or Electron Beam Sterilization on Rabbit Chondrocyte Cultures Polyglycolic acid mesh sterilized with: a) ethylene oxide or b) electron beam was seeded in six well plates with 3–4×$10^6$ cells per mesh in a total volume of 10 ml (50 ml per side) and incubated for 3–4 hr. at 37° C. in a tissue culture incubator. At this time, 1.5 ml of media were added. The seeded mesh were incubated overnight. 5 ml of media were added the next day. Media was changed three times per week for four weeks. Samples were then removed, washed with PBS, and processed for histology: hematoxylin/eosin, trichrome (for collagen); and Alcan blue (for glycosamineglycans).

6.3. Results

Figure 1:
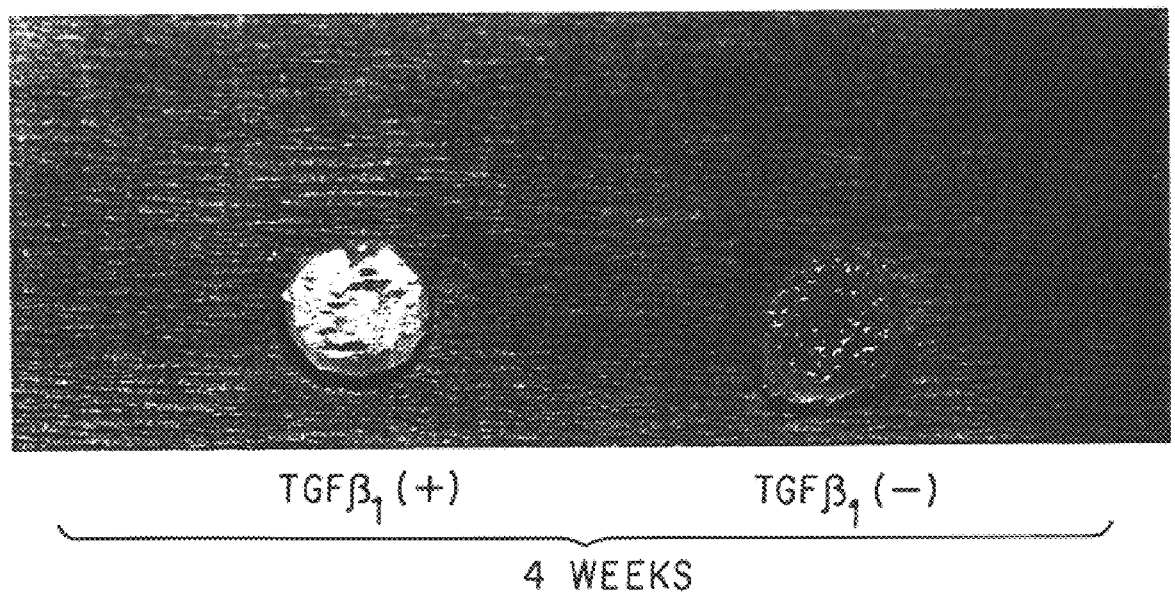
FIG. 1 is a photograph of rabbit cartilage tissue grown in vitro with or without TGF-β1.

6.3.1. Effect of Ethylene Oxide or Electron Beam Sterilization on Rabbit Chondrocyte Cultures (a) Ethylene Oxide Treated Polyglycolic Acid Mesh Chondrocytes grown in the three-dimensional matrix in the presence of TGF-β produced cartilage tissue which was smoother, more glistening and had a more solid consistency than the tissue grown in cultures without the TGF-β (FIG. 1).

Figure 2:
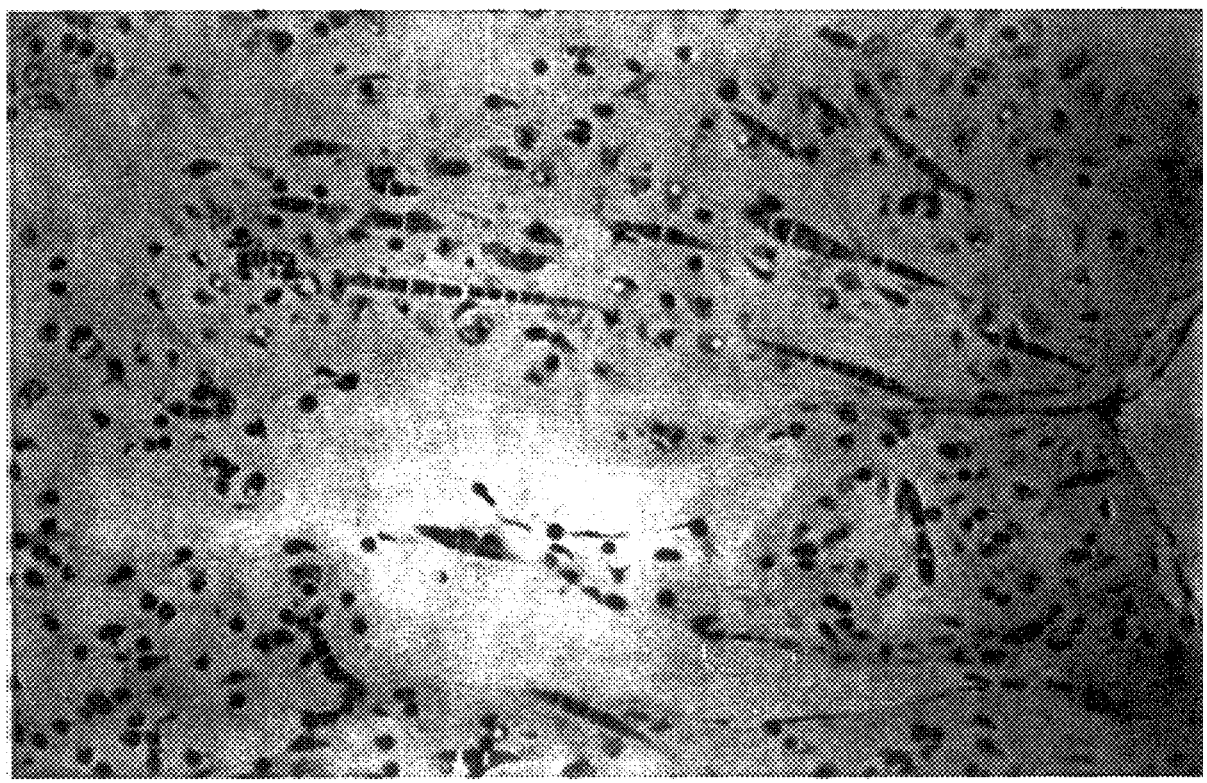
FIG. 2 is a photograph of Hematoxylin and Eosin stained cartilage tissue grown in vitro without TGF-β1.
Figure 3:
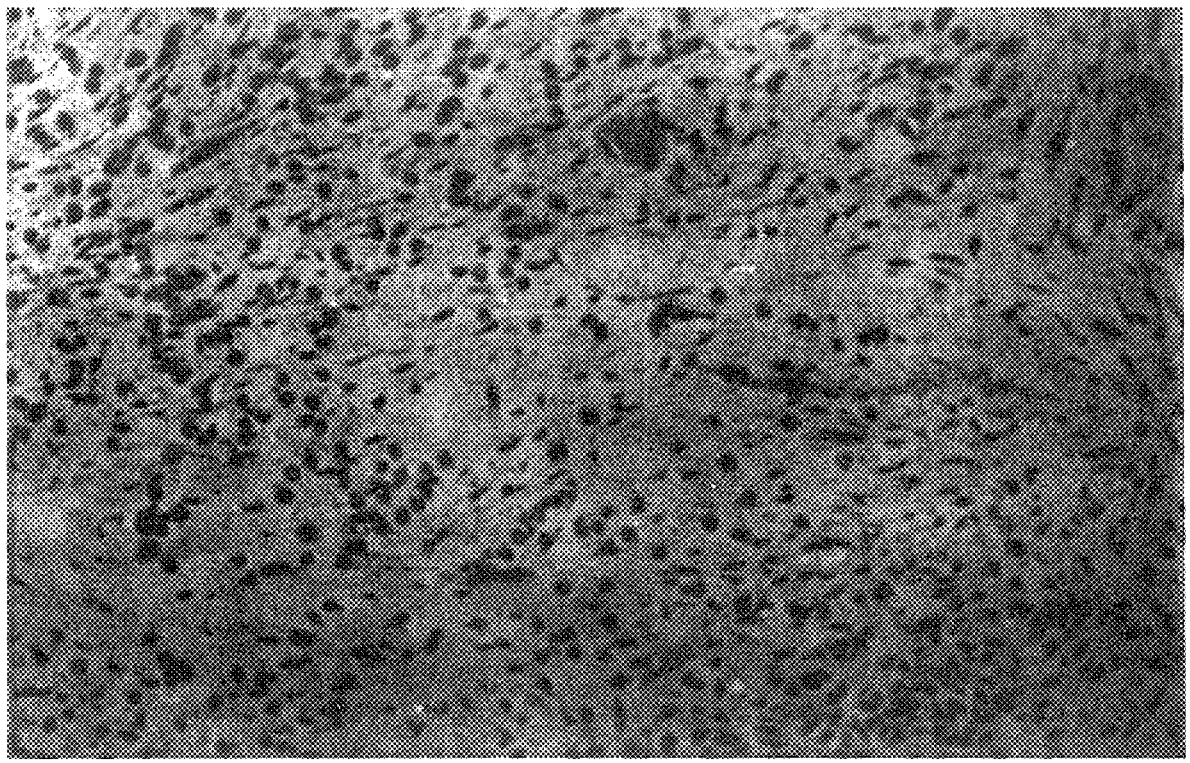
FIG. 3 is a photograph of Hematoxylin and Eosin stained cartilage tissue grown in vitro with TGF-β1.

Histological examination of the cartilage tissue using the hematoxylin-eosin stain showed an increase in cellularity in the cultures without TGF-β (FIG. 2) compared with those with TGF-β (FIG. 3).

Figure 4:
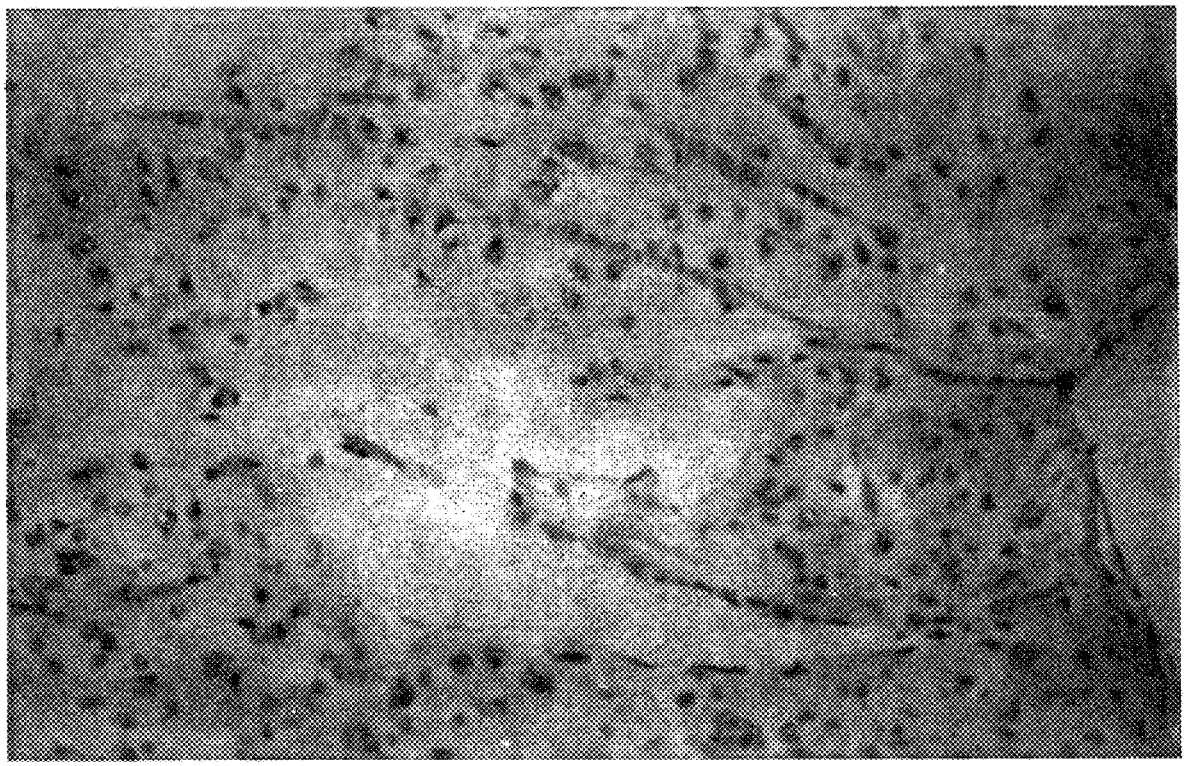
FIG. 4 is a photograph of Trichrome stained cartilage tissue grown in vitro without TGF-β1 to show the presence of collagen.
Figure 5:
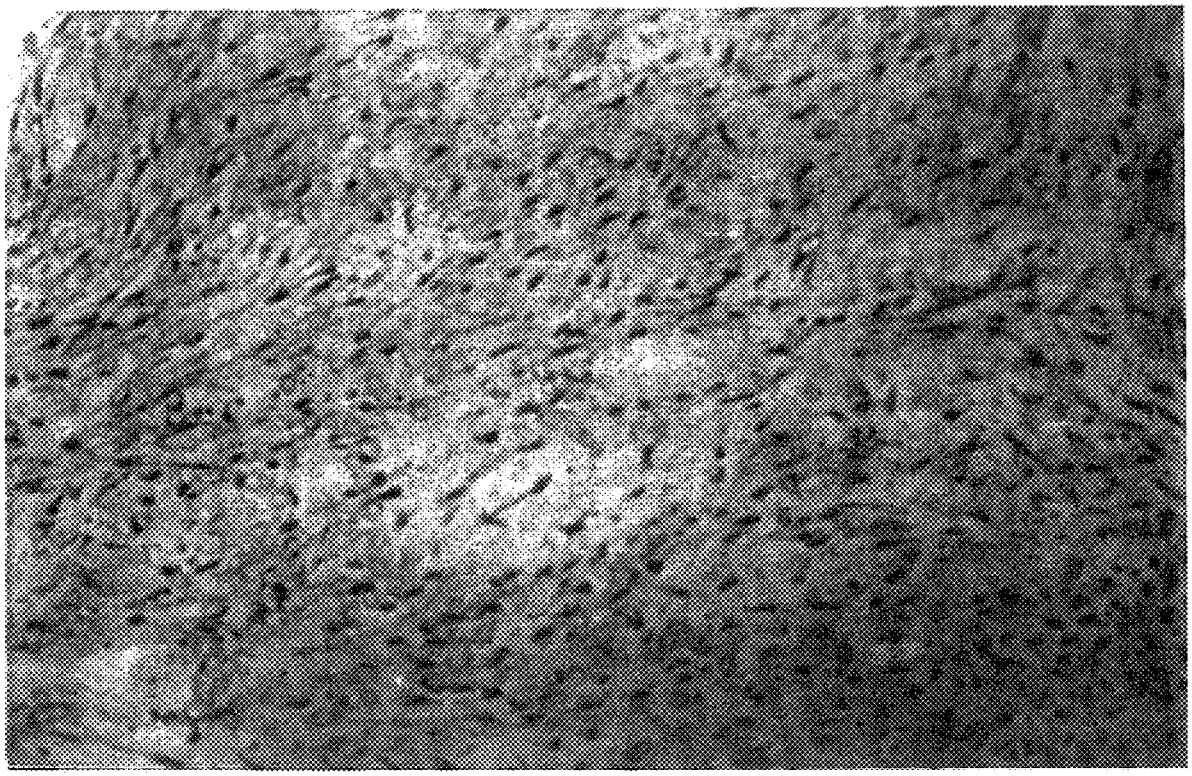
FIG. 5 is a photograph of Trichrome stained cartilage tissue grown in vitro with TGF-β1 to show the presence of collagen.

Staining with trichrome, an indicator of the presence of collagen, showed an increase in collagen deposition in cultures grown without TGF-β (FIG. 4) compared with those grown in cultures with TGF-β (FIG. 5).

Figure 6:
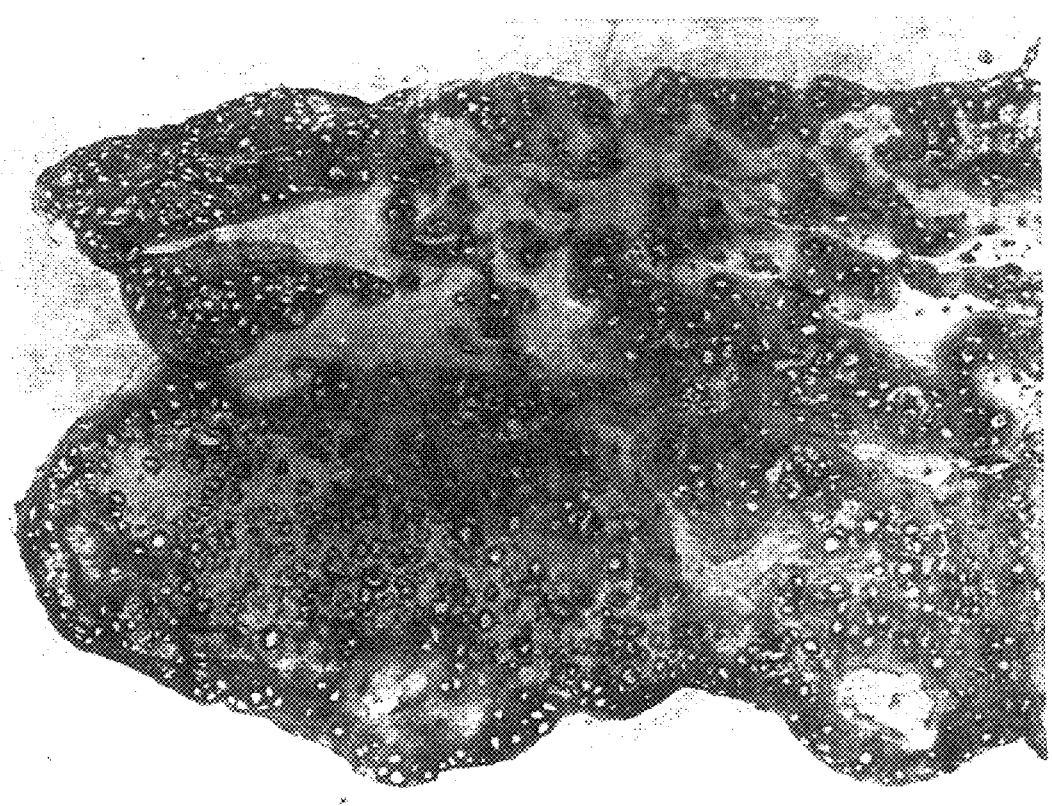
FIG. 6 is a photograph of Alcan Blue stained cartilage tissue grown in vitro without TGF-β1 to show the presence of glycosaminoglycan.
Figure 7:
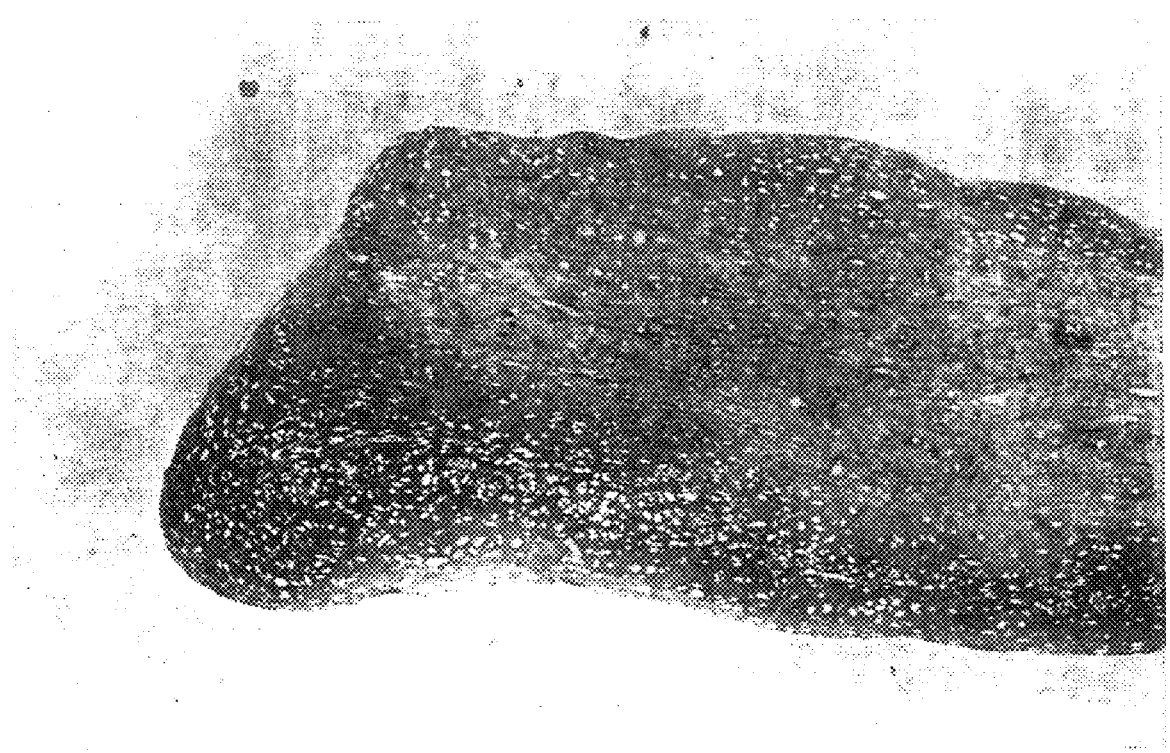
FIG. 7 is a photograph of Alcan Blue stained cartilage tissue grown in vitro with TGF-β1 to show the presence of GAG.

Alcan blue staining indicated an even distribution and increase in GAG deposition throughout the cartilage tissue when samples were grown in the presence of TGF-β (FIG. 7) compared with those without TGF-β (FIG. 6).

Figure 8:
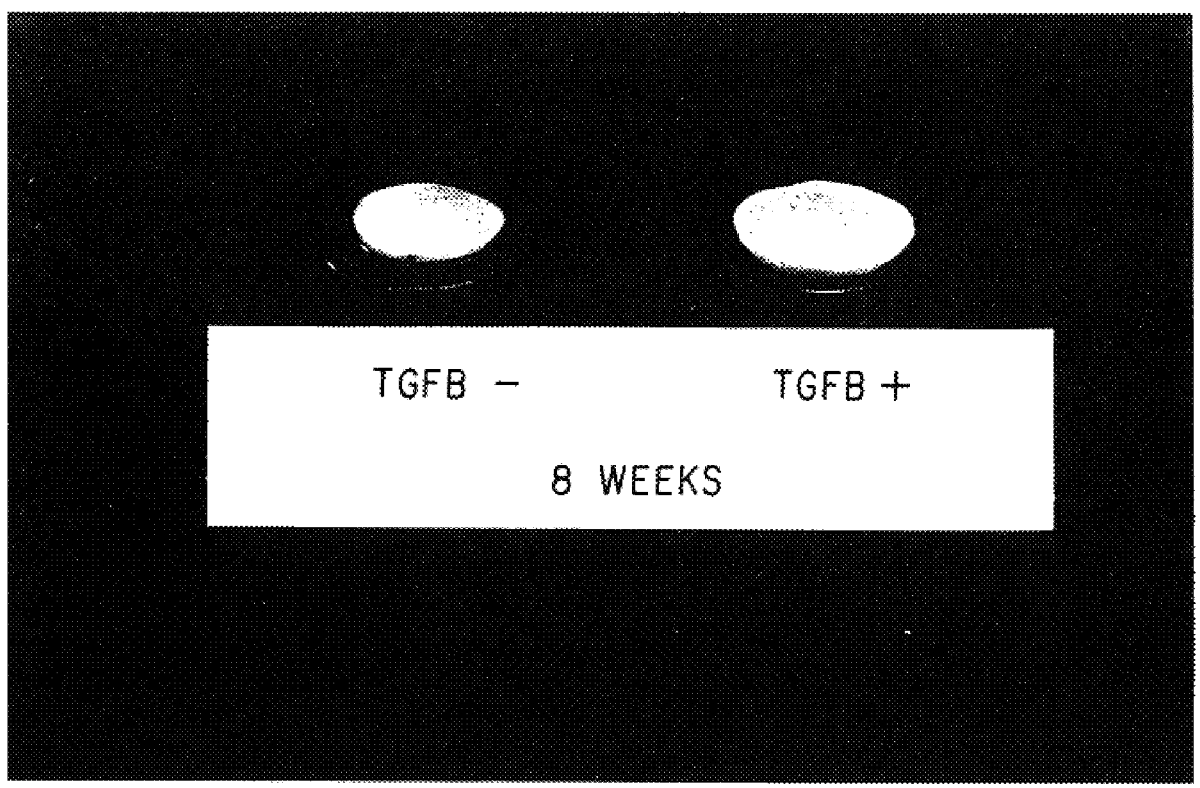
FIG. 8 is a photograph of cartilage after growth in vitro for eight weeks with or without TGF-β1.

The gross appearance of the tissue after 8 weeks indicated that the cartilage grown in the presence of TGF-β was substantially larger than that grown without TGF-β (FIG. 8).

There was a two-fold increase in the dry weight of cartilage grown in cultures containing TGF-β, 20% more collagen and 80% more GAG. See Table II below.

TABLE II

RABBIT CARTILAGE
Static: 8 Week

| Sample | Wet Weight (mg) | Dry Weight (mg) | Total Collagen (mg) | Total GAG (mg) | % Collagen (Dry Weight) | % GAG (Dry Weight) |
|---|---|---|---|---|---|---|
| + TGF-β | | | | | | |
| 1 | 64 (n = 2) | — | 4.8 | 1.4 | | |
| 2 | 73 (n = 2) | 8.2 | 6.0 | 1.1 | 73.3 | 13 |
| − TGF-β | | | | | | |
| 1 | 35 (n = 2) | — | 1.9 | 0.3 | | |
| 2 | 50 (n = 2) | 4.2 | 2.6 | 0.3 | 61.9 | 7.1 |

Normal Rabbit Cartilage:
GAG 15–40%
Collagen 55–80%

(b) Bovine chondrocytes seeded on mesh sterilized by E-beam showed poor growth after four weeks. This is most likely due to the more rapid degradation of PGA after radiation treatment, causing the cells to fall off before being able to deposit adequate extracellular matrix.

Figure 9:
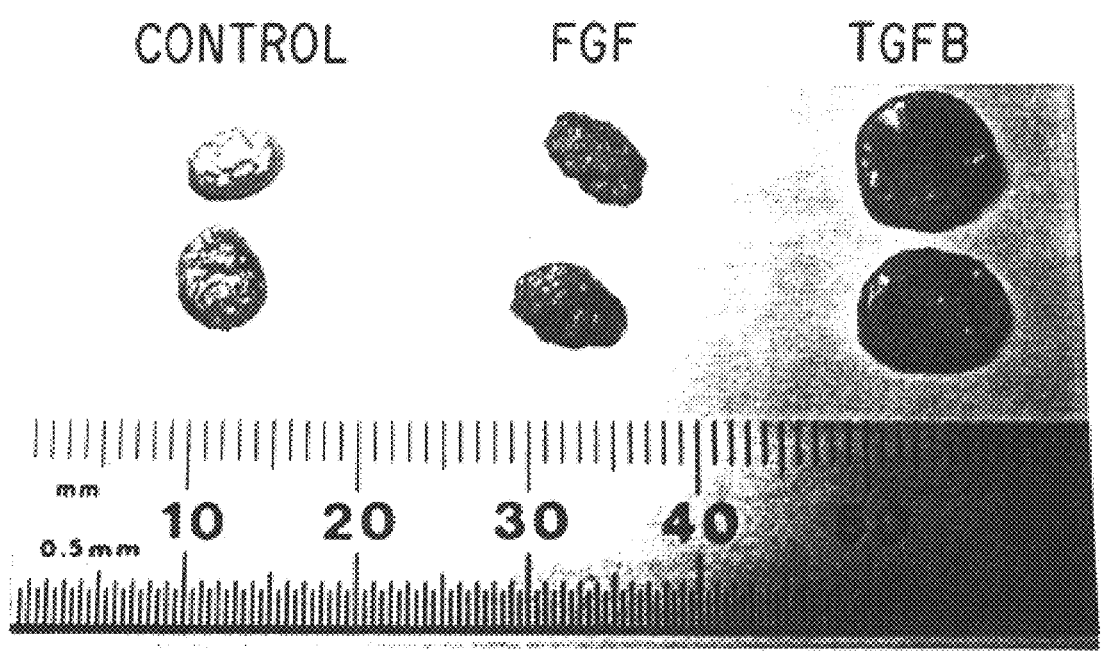
FIG. 9 is a photograph of cartilage grown on radiation sterilized mesh in control, FGF-, and TGF-β1-treated cultures of cartilage.

Addition of fibroblast growth factor B (bFGF) had no effect. However, addition of TGF-β resulted in growth of chondrocytes and formation of cartilage tissue by increasing the production of extracellular matrix by the chondrocytes. Thus, addition of TGF-β reverses the deleterious effects of sterilizing the mesh by the E-beam and enhances the production of cartilage in the three-dimensional culture matrix. (FIG. 9).

7. Effect of TGF-β on Growth of Bovine Chondrocytes in Monolayer Culture and on Three-Dimensional Frameworks With or Without Ascorbate a) Bovine chondrocytes were seeded at $2.0 \times 10^5$ cells per T-25 flask. Twenty-four hours later they were treated with ascorbate, TGF-β or both.

b) Polyglycolic acid mesh were seeded with $3 \times 10^6$ bovine chondrocytes and cultured in 6-well dishes for two days at 37° C. in complete media containing TGF-β and with 50 mg/ml ascorbate or no ascorbate.

7.1. Results 7.1.1. Effect of TGF-β on Growth of Bovine Chondrocytes in Monolayer Culture and on Three-Dimensional Frameworks With or Without Ascorbate (a) TGF-β Increases Proliferation A Bovine Chondrocytes in Monolayer FIG. 10 shows that TGF-β stimulated the growth of bovine chondrocytes in monolayer. Addition of ascorbate had a stimulating effect which was additive with TGF-β.

TGF-β treatment also resulted in substantial increase in GAG synthesis Immunoblotting with anti-type I collagen antibody was negative (FIGS. 12C and 12D).

(b) Growth of Cartilage Constructs on Three-Dimensional Frameworks

Figure 14A:
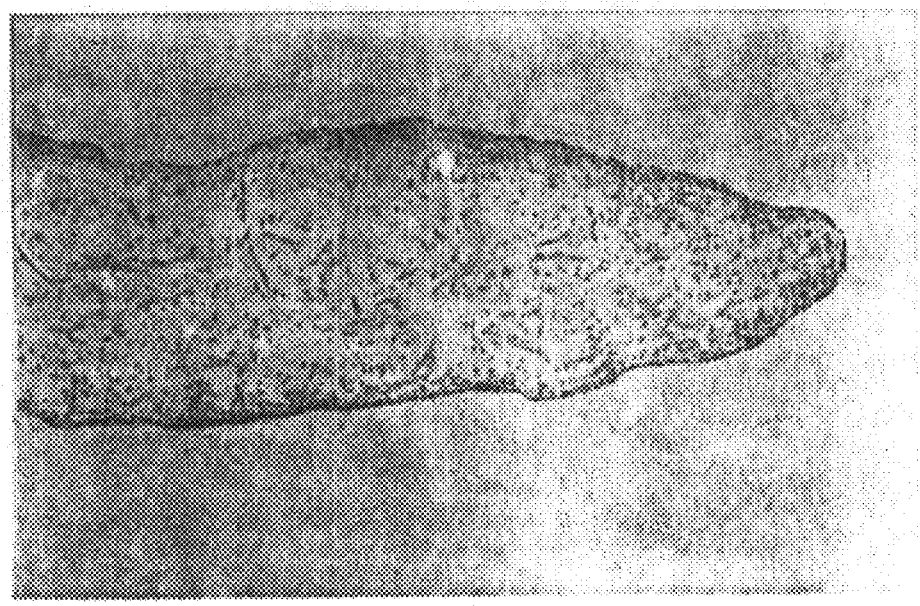
Figure 14B:
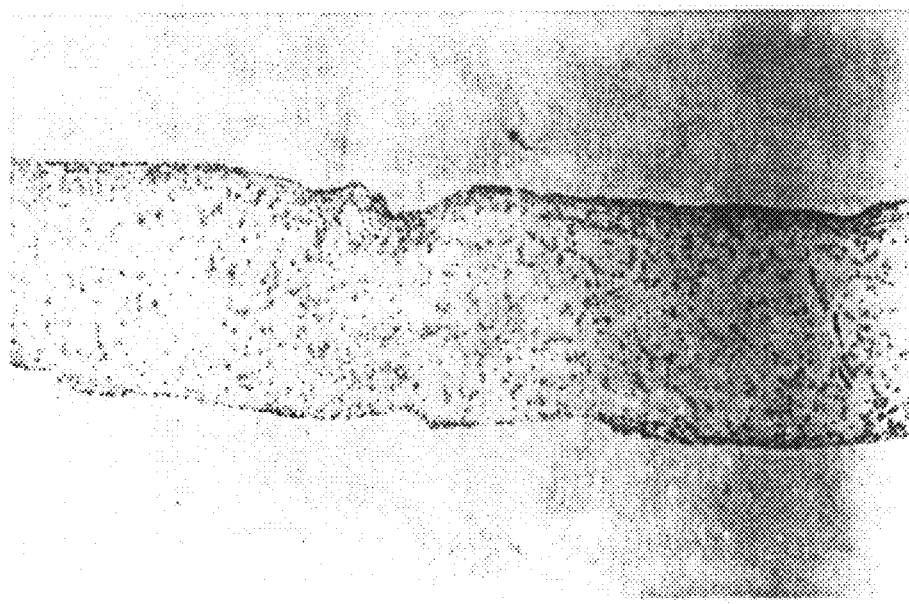
Figure 14C:
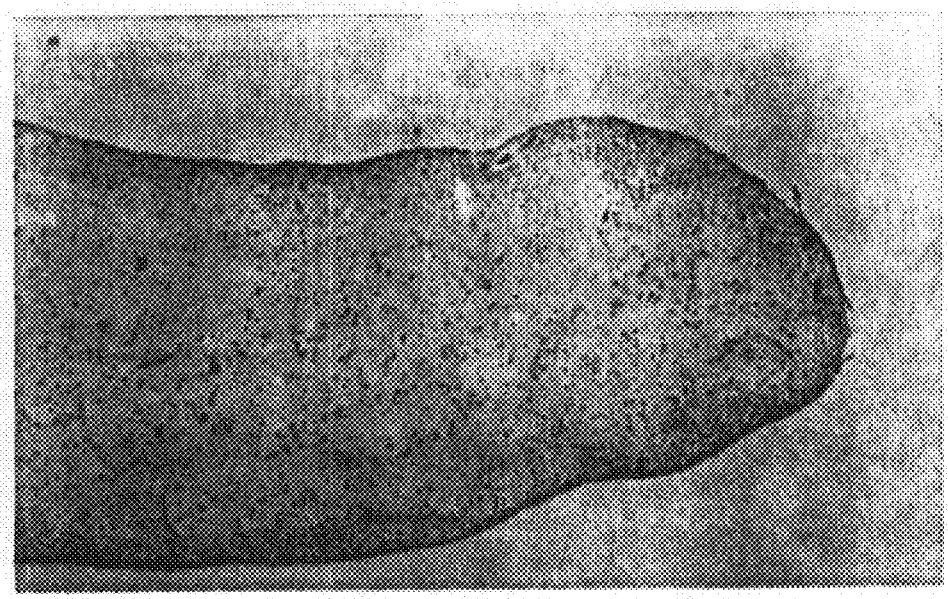
Figure 14D:
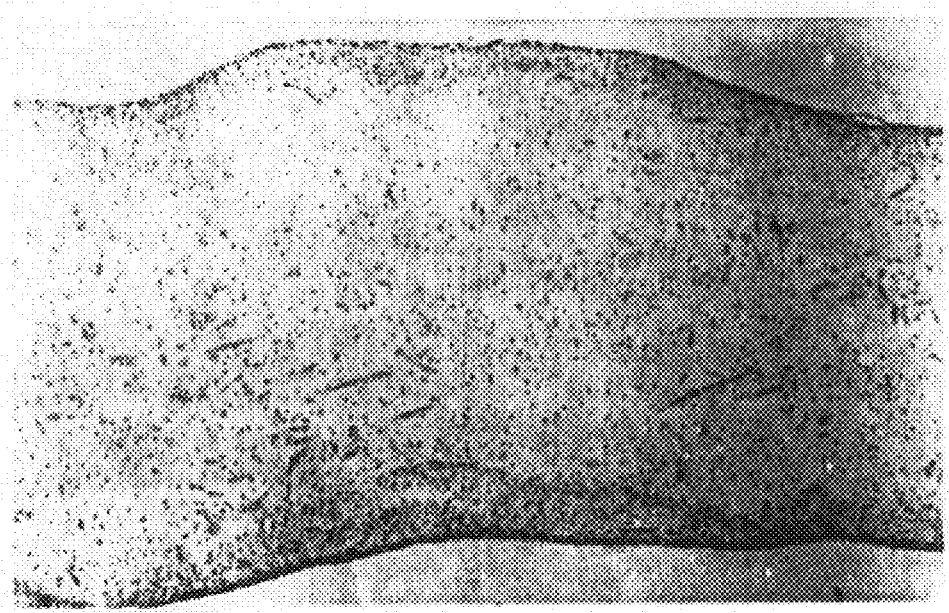

FIGS. 13A and 13B shows the cartilage constructs to be smooth and glistening and three-times larger in the presence of TGF-β (FIGS. 13A and 13B and Table III). Cells were mostly concentrated on the outside edge while the centers were less dense and contained more undegraded polyglycolic acid fibers (FIGS. 14A and 14B). Constructs stained positively for type II collagen (FIGS. 12E and F) but not for collagen type I (FIGS. 12C and D); Table III shows that TGF-β treatment resulted in about 2.5 fold increase in the dry weight of the constructs as well as in collagen and GAG.

TABLE III

BOVINE CARTILAGE

| Sample | TGF-β | Dry Weight (mg) | Total Collagen (μg) | Total GAG Content (μg) |
|---|---|---|---|---|
| 1 | − | 4.5 | 31.5 | 71.0 |
| 2 | − | 4.2 | 29.3 | 71.6 |
| 3 | − | 3.6 | 25.2 | 69.3 |
| 4 | + | 11.7 | 81.8 | 171.6 |
| 5 | + | 11.0 | 76.9 | 180.5 |
| 6 | + | 11.2 | 78.3 | 189.4 |

These results indicate that TGF-β is capable of increasing the proliferation of chondrocytes in monolayers as well as increasing cartilage production on three-dimensional frameworks.

8. Cartilage Production by Rabbit Chondrocytes on Polyglycolic Acid Frameworks in a Closed Bioreactor System Polyglycolic acid mesh were seeded with $4 \times 10^6$ cells in 6-well dishes for two days and then placed into bioreactors where they were fed continuously using a 16-channel pump (Cole-Parmer: Masterflex with computerized drive, model no. 7550-90) with complete media (250 ml for 5 bioreactors) at a flow rate of 50 μg/ml for 28 days at 37° C. with no media change. Fresh ascorbate (50 μg/ml final concentration) was added every three days. As a separate group of experiments, seeded mesh were cultured statically in 6 well dishes with 5 ml of media which was changed twice weekly. The media used for growing cells on polyglycolic acid frameworks was exactly the same as for cell growth in monolayer except for addition of ascorbate.

8.1. Results 8.1.1. Cartilage Production by Rabbit Chondrocytes on Polyglycolic Acid Frameworks in a Closed Bioreactor System FIG. 15A shows the gross appearance of seeded mesh grown statically. They were thinner than the constructs grown in the bioreactor system, which were glistening and about 2 mm in thickness. Histologic examination with Hematoxylin/Eosin or Trichrome revealed cell growth and deposition of exacellular-matrix throughout the mesh (FIGS. 16A and 16C). Alcan blue and Safranin O staining showed deposition of GAGs (FIGS. 16E–16H). Staining of constructs grown statically showed far less matrix deposition (FIGS. 16I and J). Immunostaining showed positive reactivity for type II collagen and chondroitin sulfate and no reactivity for type I collagen (FIG. 17). Cartilage produced in the bioreactors stained positively with anti-type II collagen and anti-chondroitin sulfate (FIGS. 18A and B) but not with anti-type I collagen (FIG. 18C). Biochemical analyses showed collagen and GAG values to be 15% and 25% dry weight, respectively. These values in constructs compare favorably with respective published values in rabbit articular cartilage of 30–70% and 10–30% of dry weight, respectively.

The present invention is not to be limited in scope by the specific embodiments described which are intended as single illustrations of individual aspects of the invention, and functionally equivalent methods and components are within the scope of the invention, in addition to those shown and described herein will become apparent to those skilled in the art from the foregoing description and accompanying drawings. Such modifications are intended to fall within the scope of the appended claims.

What is claimed is:

1. A method for preparing a living stromal tissue in vitro, comprising culturing mesenchymal stem cells inoculated onto a three-dimensional framework in a nutrient medium, so that the mesenchymal stem cells and connective tissue proteins naturally secreted by the mesenchymal stem cells attach to and substantially envelope the framework composed of a biocompatible, non-living material formed into a three dimensional structure having interstitial spaces bridged by the mesenchymal stem cells.

2. The method of claim 1 in which the mesenchymal stem cells are derived from umbilical cord cells, placental cells or bone marrow cells from umbilical cord blood.

3. The method of claim 1 in which the framework is composed of a biodegradable material.

4. The method of claim 3 in which the biodegradable material is polyglycolic acid, cotton, cat gut sutures, cellulose, gelatin, collagen or polyhydroxyalkanoates.

5. The method of claim 1 in which the framework is treated with ethylene oxide.

6. The method of claim 1 in which the framework is treated with an electron beam.

7. The method of claim 1 in which the framework is composed of a non-biodegradable material.

8. The method of claim 7 in which the non-biodegradable material is a polyamide, a polyester, a polystyrene, a polypropylene, a polyacrylate, a polyvinyl, a polycarbonate, a polytetrafluorethylene, or a nitrocellulose compound.

9. The method of claim 1 in which the framework is a mesh.

10. The method of claim 1 in which the framework is a sponge.

11. A living stromal tissue prepared in vitro, comprising mesenchymal stem cells and connective tissue proteins naturally secreted by the mesenchymal stem cells attached to and substantially enveloping a three-dimensional framework composed of a biocompatible, non-living material formed into a three-dimensional structure having interstitial spaces bridged by the mesenchymal stem cells.

12. The living stromal tissue of claim 11 in which the mesenchymal stem cells are derived from umbilical cord cells, placental cells or bone marrow cells from umbilical cord blood.

13. The living stromal tissue of claim 11 in which the framework was treated with ethylene oxide.

14. The living stromal tissue of claim 11 in which the framework was treated with an electron beam.

15. The living stromal tissue of claim 11 in which the framework is composed of a biodegradable material.

16. The living stromal tissue of claim 15 in which the biodegradable material is polyglycolic acid, cotton, cat gut sutures, cellulose, gelatin, collagen or polyhydroxyalkanoates.

17. The living stromal tissue of claim 11 in which the framework is composed of a non-biodegradable material.

18. The living stromal tissue of claim 17 in which the non-biodegradable material is a polyamide, a polyester, a polystyrene, a polypropylene, a polyacrylate, a polyvinyl, a polycarbonate, a polytetrafluorethylene, or a nitrocellulose compound.

19. The living stromal tissue of claim 11 in which the framework is a mesh.

20. The living stromal tissue of claim 11 in which the framework is a sponge.

* * * * *